United States Patent
Shaber et al.

(10) Patent No.: US 6,313,147 B1
(45) Date of Patent: Nov. 6, 2001

(54) HETEROCYCLIC SUBSTITUTED ISOXAZOLIDINES AND THEIR USE AS FUNGICIDES

(75) Inventors: Steven Howard Shaber, Horsham, PA (US); Lixin Zhang, Shenyang (CN); Edward Michael Szapacs, Center Valley; James Allen Quinn, North Wales, both of PA (US)

(73) Assignee: Dow Agrosciences LLC, Indianapolis, IN (US)

( * ) Notice: Subject to any disclaimer, the term of this patent is extended or adjusted under 35 U.S.C. 154(b) by 0 days.

(21) Appl. No.: 09/520,736

(22) Filed: Mar. 8, 2000

Related U.S. Application Data

(60) Provisional application No. 60/123,783, filed on Mar. 11, 1999.

(51) Int. Cl.⁷ .......................... C07D 413/04; A01N 43/40
(52) U.S. Cl. .......................................... 514/340; 546/272.1
(58) Field of Search .......................... 514/340; 546/272.1

(56) References Cited

U.S. PATENT DOCUMENTS

| 4,066,770 | 1/1978 | Boyce et al. | 424/263 |
| 4,239,889 | 12/1980 | ten Haken et al. | 544/335 |

Primary Examiner—Jane Fan

(57) ABSTRACT

Compounds with fungicidal properties having formula

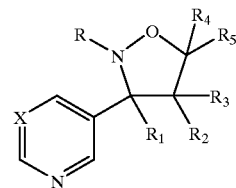

I

X is CH or nitrogen; R is $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$alkynyl, $(C_1-C_{12})$alkoxy$(C_1-C_{12})$alkyl, $(C_3-C_7)$cycloalkyl, halo$(C_3-C_7)$cycloalkyl, $(C_3-C_7)$cycloalkyl$(C_1-C_4)$alkyl, aralkyl, aryloxy$(C_1-C_4)$alkyl or heterocyclic; $R_1$ is aryl, heterocyclic or $C(R_6R_7R_8)$. $R_2$ and $R_3$ are each selected from hydrogen, $(C_1-C_{12})$alkyl, halo$(C_1-C_{12})$alkyl, $(C_1-C_{12})$alkoxy, halo$(C_1-C_{12})$alkoxy, $(C_3-C_7)$cycloalkyl, $(C_3-C_7)$cycloalkyl$(C_1-C_4)$alkyl, aryl, aralkyl, heterocyclic; cyano, and $(C_1-C_4)$alkoxycarbonyl; $R_4$ and $R_5$ are each selected from hydrogen, $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$alkynyl, $(C_3-C_7)$cycloalkyl, halo$(C_3-C_7)$cycloalkyl, $(C_3-C_7)$cycloalkyl$(C_1-C_4)$alkyl, aryl, aryloxy$(C_1-C_4)$alkyl, aralkyl, heterocyclic, cyano, and $(C_1-C_4)$alkoxycarbonyl such that $R_4$ and $R_5$ are not both hydrogen; $R_6$, $R_7$, and $R_8$ are each selected from hydrogen, $(C_1-C_{12})$alkyl, $(C_2-C_8)$alkenyl, $(C_2-C_8)$alkynyl, $(C_1-C_{12})$alkoxy$(C_1-C_{12})$alkyl, $(C_3-C_7)$cycloalkyl, $(C_3-C_7)$cycloalkyl$(C_1-C_4)$alkyl, aryl, aralkyl, and heterocyclic$(C_1-C_4)$alkyl.

10 Claims, No Drawings

HETEROCYCLIC SUBSTITUTED ISOXAZOLIDINES AND THEIR USE AS FUNGICIDES

This application claims benefit of No. 60/123,783 Mar. 11, 1999 under 35 USC 119(e).

The present invention relates to heterocyclic substituted isoxazolidines compounds, compositions containing these compounds and methods for controlling fungi by the use of a fungitoxic amount of these compounds.

It is known that certain. 2-aryl-3-(3'-pyridyl) isoxazolidines, U.S. Pat. No. 4,066,770, are useful as fungicides.

We have discovered novel isoxazolidine derivatives which possess 3,3'-disubstitution, one of which is a 3-pyridyl or 5-pyrimidinyl, and the other of which is a non-hydrogen bearing substituent and additionally at C-5 at least one carbon bearing substituent.

The novel heterocyclic substituted isoxazolidine compounds of the present invention have the Formula (I)

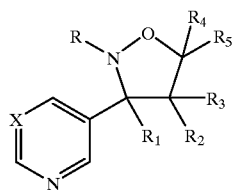

X is CH or nitrogen;

R is selected from the group consisting of $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$alkynyl, $(C_1-C_{12})$alkoxy$(C_1-C_{12})$alkyl, $(C_3-C_7)$cycloalkyl, halo$(C_3-C_7)$cycloalkyl, $(C_3-C_7)$cycloalkyl$(C_1-C_4)$ alkyl, aralkyl, aryloxy$(C_1-C_4)$alkyl and heterocyclic $R_1$ is selected from the group consisting of aryl, heterocyclic and $C(R_6R_7R_8)$.

$R_2$ and $R_3$ are each independently selected from the group consisting of $(C_1-C_{12})$alkyl, halo$(C_1-C_{12})$alkyl, $(C_1-C_{12})$alkoxy, halo$(C_1-C_{12})$alkoxy, $(C_3-C_7)$ cycloalkyl, $(C_3-C_7)$cycloalkyl$(C_1-C_4)$alkyl, aryl, aralkyl, heterocyclic, cyano, and $(C_1-C_4)$ alkoxycarbonyl;

$R_4$ and $R_5$ are each selected from the group consisting of $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$ alkynyl, $(C_3-C_7)$cycloalkyl, halo$(C_3-C_7)$cycloalkyl, $(C_3-C_7)$cycloalkyl$(C_1-C_4)$alkyl, aryl, aryloxy$(C_1-C_4)$ alkyl, aralkyl, heterocyclic, cyano, and $(C_1-C_4)$ alkoxycarbonyl such that $R_4$ and $R_5$ are not both hydrogen;

$R_6$, $R_7$, and $R_8$ are each independently selected from the group consisting of hydrogen, $(C_1-C_{12})$alkyl, $(C_2-C_8)$ alkenyl, $(C_2-C_8)$alkynyl, $(C_1-C_{12})$alkoxy$(C_1-C_{12})$ alkyl, $(C_3-C_7)$cycloalkyl, $(C_3-C_7)$cycloalkyl$(C_1-C_4)$ alkyl, aryl, aralkyl, and heterocyclic$(C_1-C_4)$alkyl;

The aforementioned $(C_1-C_{12})$alkyl, $(C_2-C_8)$alkenyl, $(C_2-C_8)$alkynyl and $(C_3-C_7)$cycloalkyl groups may be optionally substituted with up to three substituents selected from the group consisting of nitro, trihalomethyl and cyano.

The term alkyl includes both branched and straight chained alkyl groups from 1 to 12 carbon atoms. Typical alkyl groups are methyl, ethyl, n-propyl, iso-propyl, n-butyl, sec-butyl, isobutyl, t-butyl, n-pentyl, isopentyl, n-hexyl, n-heptyl, isooctyl, nonyl, decyl, undecyl, dodecyl and the like. The term haloalkyl refers to an alkyl group substituted with 1 to 3 halogens.

The term alkenyl refers to an ethylenically unsaturated hydrocarbon group, straight or branched, having a chain length of 2 to 12 carbon atoms and 1 or 2 ethylenic bonds. The term haloalkenyl refers to an alkenyl group substituted with 1 to 3 halogen atoms. The term alkynyl refers to an unsaturated hydrocarbon group, straight or branched, having a chain length of 2 to 12 carbon atoms and 1 or 2 acetylenic bonds.

The term cycloalkyl refers to a saturated ring system having 3 to 7 carbon atoms. The term aryl is understood to be phenyl or napthyl, which maybe further substituted with up to three substituents selected from the group consisting of halogen, cyano, nitro, trihalomethyl, phenyl, phenoxy, $(C_1-C_4)$alkyl, $(C_1-C_4)$alkylthio, $(C_1-C_4)$alkylsulfoxide $(C_1-C_6)$alkoxy and halo$(C_1-C_4)$alkyl.

Typical aryl substituents include but are not limited to 4-chlorophenyl, 4-fluoro-phenyl, 4-bromophenyl, 2-methoxyphenyl, 2-methylphenyl, 3-methyphenyl, 4-methyl-phenyl, 2,4-dibromophenyl, 3,5-difluorophenyl, 2,4,6-trichlorophenyl, 4-methoxy-phenyl, 2-chloronapthyl, 2,4-dimethoxyphenyl, 4-(trifluoromethyl)phenyl and 2-iodo-4-methylphenyl.

The term heterocyclic refers to a substituted or unsubstituted 5 or 6 membered unsaturated ring containing one, two or three heteroatoms, preferably one or two heteroatoms selected from oxygen, nitrogen and sulfur; or is a bicyclic unsaturated ring system containing up to 10 atoms including one heteratom selected from oxygen, nitrogen and sulfur. Examples of heterocycles include, but are not limited to, 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and iso-quinolyl. The heterocyclic ring may be optionally substituted with up to two substituents independently selected from $(C_1-C_4)$alkyl, halogen, cyano, nitro and trihalomethyl.

The term aralkyl is used to describe a group wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chloro-phenyl)ethyl, 2-(3-chlorophenyl) ethyl, 2-(4-chlorophenyl)ethyl, 2-(2-fluorophenyl)-ethyl, 2-(3-fluorophenyl)ethyl, 2-(4-fluorophenyl)ethyl, 2-(2-methylphenyl)ethyl, 2-(3-methylphenyl)ethyl, 2-(4-methylphenyl)ethyl, 2-(4-trifluoromethylphenyl)ethyl, 2-(2-methoxyphenyl)ethyl, 2-(3-methoxyphenyl)ethyl, 2-(4-methoxyphenyl)ethyl, 2-(2,4-dichlorophenyl)ethyl, 2-(3,5-dimethoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichlorophenyl)propyl, 3-(2-fluorophenyl)propyl, 3-(3-fluorophenyl)propyl, 3-(4-fluorophenyl)propyl, 3-(2-methylphenyl)propyl, 3-(3-methylphenyl)propyl, 3-(4-methylphenyl)ethyl, 3-(2-methoxyphenyl)propyl, 3-(3-methoxyphenyl)propyl, 3-(4-methoxyphenyl)propyl, 3-(4-trifluoromethylphenyl)propyl, 3-(2,4-dichlorophenyl)propyl and 3-(3,5-dimethoxyphenyl)propyl.

Typical phenbutyl moieties include are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl) butyl, 4-(3-methylphenyl)-butyl, 4-(4-methylphenyl)butyl, 4-(2,4-dichlorophenyl)butyl, 4-(2-methoxphenyl)butyl, 4-(3-methoxyphenyl)butyl and 4-(4-methoxyphenyl)butyl.

Halogen or halo is defined as iodo, fluoro, bromo and chloro moieties.

Those skilled in the art will recognize the groups $R_2$, $R_3$ and $R_4$, $R_5$ can exist as cis or trans isomers relative to the heterocyclic ring and $R_1$ at C-3. These isomers can be separated into individual components by conventional means. Both the individual isomeric compounds and mixtures thereof form subjects of the invention and have fungicidal properties.

A preferred embodiment of this invention are the compounds, enantiomorphs, salts and complexes of Formula (I') wherein $R_2$, $R_3$, $R_5$ are hydrogen, $R_1$ is aryl or $C(R_6R_7R_8)$, R is $(C_1-C_{12})$alkyl and $R_4$ is independently aryl, aryloxy$(C_1-C_4)$alkyl, aralkyl, heterocyclic cyano, or $(C_1-C_4)$alkoxycarbonyl.

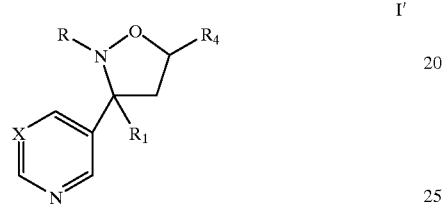

I'

A more preferred embodiment of this invention are the compounds, enantiomorphs, salts and complexes of Formula (I") wherein X is CH, R is methyl and $R_1$ is $C(R_6R_7R_8)$ in which $R_6$, $R_7$, and $R_8$ are hydrogen.

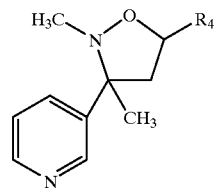

I"

Typical compounds encompassed by the present invention of Formula I include those compounds presented in Table 1 of Formula II wherein X is CH, $R_2$ and $R_3$ are hydrogen, $R_1$ is $C(R_6R_7R_8)$ wherein $R_4$, $R_5$, $R_6$, $R_7$, and $R_8$ are defined in Table 1.

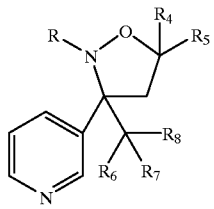

(II)

TABLE I

| Cmpd # | R | $R_4$ | $R_5$ | $R_6$ | $R_7$ | $R_8$ | Physical Property |
|---|---|---|---|---|---|---|---|
| 1.1 | $CH_3$ | Ph | H | H | H | H | oil |
| 1.2 | $CH_3$ | 2-Cl(Ph) | H | H | H | H | oil |
| 1.3 | $CH_3$ | 3-Cl(Ph) | H | H | H | H | oil |
| 1.4 | $CH_3$ | 4-Cl(Ph) | H | H | H | H | oil |
| 1.4A | $CH_3$ | 4-Cl(Ph) | H | H | H | H | oil, isomer A |
| 1.4B | $CH_3$ | 4-Cl(Ph) | H | H | H | H | 75–80° C. |
| 1.5 | $CH_3$ | 2-F(Ph) | H | W | H | H | oil |
| 1.6 | $CH_3$ | 3-F(Ph) | H | H | H | H | oil |
| 1.7 | $CH_3$ | 4-F(Ph) | H | H | H | H | oil |
| 1.8 | $CH_3$ | 2-Br(Ph) | H | H | H | H | |
| 1.9 | $CH_3$ | 3-Br(Ph) | H | H | H | H | oil |
| 1.10 | $CH_3$ | 4-Br(Ph) | H | H | H | H | oil |
| 1.11 | $CH_3$ | 2-$CF_3$(Ph) | H | H | H | H | |
| 1.12 | $CH_3$ | 3-$CF_3$(Ph) | H | H | H | H | |
| 1.13 | $CH_3$ | 4-$CF_3$(Ph) | H | H | H | H | oil |
| 1.14 | $CH_3$ | 2-$CH_3$(Ph) | H | H | H | H | |
| 1.15 | $CH_3$ | 3-$CH_3$(Ph) | H | H | H | H | oil |
| 1.16 | $CH_3$ | 4-$CH_3$(Ph) | H | H | H | H | |
| 1.17 | $CH_3$ | 2-$OCH_3$(Ph) | H | H | H | H | |
| 1.18 | $CH_3$ | 3-$OCH_3$(Ph) | H | H | H | H | |
| 1.19 | $CH_3$ | 4-$OCH_3$(Ph) | H | H | H | H | |
| 1.20 | $CH_3$ | 1-Naphthyl | H | H | H | H | |
| 1.21 | $CH_3$ | 2,4-Cl(Ph) | H | H | H | H | |
| 1.22 | $CH_3$ | 3,4-Cl(Ph) | H | H | H | H | |
| 1.23 | $CH_3$ | 2,4-$CH_3$(Ph) | H | H | H | H | oil |
| 1.23A | $CH_3$ | 2,4-$CH_3$(Ph) | H | H | H | H | oil |
| 1.24 | $CH_3$ | 2-Pyridyl | H | H | H | H | |
| 1.25 | $CH_3$ | 3-Pyridyl | H | H | H | H | |
| 1.26 | $CH_3$ | 4-Pyridyl | H | H | H | H | |
| 1.27 | $CH_3$ | $CH_2$—O(Ph) | H | H | H | H | |
| 1.28 | $CH_3$ | $CH_2$—O(2-Cl(Ph)) | H | H | H | H | |
| 1.29 | $CH_3$ | $CH_2$—O(3-Cl(Ph)) | H | H | H | H | |
| 1.30 | $CH_3$ | $CH_2$—O(4-Cl(Ph)) | H | H | H | H | |
| 1.31 | $CH_3$ | $CH_2$—O(2-F(Ph)) | H | H | H | H | |
| 1.32 | $CH_3$ | $CH_2$—O(3-F(Ph)) | H | H | H | H | |
| 1.33 | $CH_3$ | $CH_2$—O(4-F(Ph)) | H | H | H | H | |
| 1.34 | $CH_3$ | $CH_2$—O(3-$CF_3$(Ph)) | H | H | H | H | |
| 1.35 | $CH_3$ | $CH_2$—O(4-$CF_3$(Ph)) | H | H | H | H | |
| 1.36 | $C_2H_5$ | Ph | H | H | H | H | |

TABLE I-continued

| Cmpd # | R | R4 | R5 | R6 | R7 | R8 | Physical Property |
|---|---|---|---|---|---|---|---|
| 1.37 | C2H5 | 2Cl(Ph) | H | H | H | H | |
| 1.38 | C2H5 | 3Cl(Ph) | H | H | H | H | |
| 1.39 | C2H5 | 4Cl(Ph) | H | H | H | H | oil |
| 1.40 | C2H5 | 2,4-Cl(Ph) | H | H | H | H | |
| 1.41 | C2H5 | 3,4-Cl(Ph) | H | H | H | H | |
| 1.42 | C2H5 | 2-Pyridyl | H | H | H | H | |
| 1.43 | C2H5 | 3-Pyridyl | H | H | H | H | |
| 1.44 | C2H5 | 4-Pyridyl | H | H | H | H | |
| 1.45 | C2H5 | —CH2—OPh | H | H | H | H | |
| 1.46 | C2H5 | CH2—O-(4-Cl(Ph)) | H | H | H | H | |
| 1.47 | C2H5 | CH2—O(4-CF3(Ph)) | H | H | H | H | |
| 1.48 | iso-C3H7 | Ph | H | H | H | H | |
| 1.49 | iso-C3H7 | 2-Cl(Ph) | H | H | H | H | |
| 1.50 | iso-C3H7 | 3-Cl(Ph) | H | H | H | H | |
| 1.51 | iso-C3H7 | 4-Cl(Ph) | H | H | H | H | oil |
| 1.52 | iso-C3H7 | 2,4-Cl(Ph) | H | H | H | H | |
| 1.53 | iso-C3H7 | 3,4-Cl(Ph) | H | H | H | H | |
| 1.54 | iso-C3H7 | 2-Pyridyl | H | H | H | H | |
| 1.55 | iso-C3H7 | 3-Pyridyl | H | H | H | H | |
| 1.56 | iso-C3H7 | 4-Pyridyl | H | H | H | H | |
| 1.57 | iso-C3H7 | CH2—OPh | H | H | H | H | |
| 1.58 | iso-C3H7 | CH2—O-(4-Cl(Ph)) | H | H | H | H | |
| 1.59 | iso-C3H7 | CH2—O(4-CF3(Ph)) | H | H | H | H | |
| 1.60 | c-C6H11 | Ph | H | H | H | H | |
| 1.61 | c-C6H11 | 2-Cl(Ph) | H | H | H | H | |
| 1.62 | c-C6H11 | 3-Cl(Ph) | H | H | H | H | |
| 1.63 | c-C6H11 | 4-Cl(Ph) | H | H | H | H | oil |
| 1.65 | c-C6H11 | 2,4-Cl(Ph) | H | H | H | H | |
| 1.64 | c-C6H11 | 3,4-Cl(Ph) | H | H | H | H | |
| 1.66 | c-C6H11 | 2-Pyridyl | H | H | H | H | |
| 1.67 | c-C6H11 | 3-Pyridyl | H | H | H | H | |
| 1.68 | c-C6H11 | 4-Pyridyl | H | H | H | H | |
| 1.69 | c-C6H11 | CH2—OPh | H | H | H | H | |
| 1.70 | c-C6H11 | CH2—O-(4-Cl(Ph)) | H | H | H | H | |
| 1.71 | c-C6H11 | CH2—O(4-CF3(Ph)) | H | H | H | H | |
| 1.72 | CH3 | Ph | H | CH3 | H | H | |
| 1.73 | CH3 | 2-Cl(Ph) | H | CH3 | H | H | |
| 1.74 | CH3 | 3-Cl(Ph) | H | CH3 | H | H | |
| 1.75 | CH3 | 4-Cl(Ph) | H | CH3 | H | H | |
| 1.76 | CH3 | 2,4-Cl(Ph) | H | CH3 | H | H | |
| 1.77 | CH3 | 3,4-Cl(Ph) | H | CH3 | H | H | |
| 1.78 | CH3 | 2-Pyridyl | H | CH3 | H | H | |
| 1.79 | CH3 | 3-Pyridyl | H | CH3 | H | H | |
| 1.80 | CH3 | 4-Pyridyl | H | CH3 | H | H | |
| 1.81 | CH3 | CH2—OPh | H | CH3 | H | H | |
| 1.82 | CH3 | CH2—O(2-Cl(Ph)) | H | CH3 | H | H | |
| 1.83 | CH3 | CH2—O(3-Cl(Ph)) | H | CH3 | H | H | |
| 1.84 | CH3 | CH2—O(4-Cl(Ph)) | H | CH3 | H | H | |
| 1.85 | CH3 | CH2—O(2-F(Ph)) | H | CH3 | H | H | |
| 1.86 | CH3 | CH2—O(3-F(Ph)) | H | CH3 | H | H | |
| 1.87 | CH3 | CH2—O(4-F(Ph)) | H | CH3 | H | H | |
| 1.88 | CH3 | CH2—O(2-CF3(Ph)) | H | CH3 | H | H | |
| 1.89 | CH3 | CH2—O(3-CF3(Ph)) | H | CH3 | H | H | |
| 1.90 | CH3 | CH2—O(4-CF3(Ph)) | H | CH3 | H | H | |
| 1.91 | C2H5 | Ph | H | CH3 | H | H | |
| 1.89 | C2H5 | 2-Cl(Ph) | H | CH3 | H | H | |
| 1.90 | C2H5 | 3-Cl(Ph) | H | CH3 | H | H | |
| 1.91 | C2H5 | 4-Cl(Ph) | H | CH3 | H | H | |
| 1.92 | C2H5 | 2,4-Cl(Ph) | H | CH3 | H | H | |
| 1.93 | C2H5 | 3,4-Cl(Ph) | H | CH3 | H | H | |
| 1.94 | C2H5 | 2-Pyridyl | H | CH3 | H | H | |
| 1.95 | C2H5 | 3-Pyridyl | H | CH3 | H | H | |
| 1.96 | C2H5 | 4-Pyridyl | H | CH3 | H | H | |
| 1.97 | C2H5 | CH2—OPh | H | CH3 | H | H | |
| 1.98 | C2H5 | CH2—O-(4-Cl(Ph)) | H | CH3 | H | H | |
| 1.99 | C2H5 | CH2—O(4-CF3(Ph)) | H | CH3 | H | H | |
| 1.100 | iso-C3H7 | Ph | H | CH3 | H | H | |
| 1.100 | iso-C3H7 | 2-Cl(Ph) | H | CH3 | H | H | |
| 1.101 | iso-C3H7 | 3-Cl(Ph) | H | CH3 | H | H | |
| 1.102 | iso-C3H7 | 4-Cl(Ph) | H | CH3 | H | H | |
| 1.103 | iso-C3H7 | 2,4-Cl(Ph) | H | CH3 | H | H | |
| 1.104 | iso-C3H7 | 3,4-Cl(Ph) | H | CH3 | H | H | |
| 1.105 | iso-C3H7 | 2-Pyridyl | H | CH3 | H | H | |
| 1.106 | iso-C3H7 | 3-Prridyl | H | CH3 | H | H | |
| 1.107 | iso-C3H7 | 4-Pyridyl | H | CH3 | H | H | |
| 1.108 | iso-C3H7 | CH2—OPh | H | CH3 | H | H | |
| 1.109 | iso-C3H7 | CH2—O-(4-Cl(Ph)) | H | CH3 | H | H | |

TABLE I-continued

| Cmpd # | R | $R_4$ | $R_5$ | $R_6$ | $R_7$ | $R_8$ | Physical Property |
|---|---|---|---|---|---|---|---|
| 1.110 | iso-$C_3H_7$ | $CH_2$—O(4-$CF_3$(Ph)) | H | $CH_3$ | H | H | |
| 1.111 | c-$C_6H_{11}$ | Ph | H | $CH_3$ | H | H | |
| 1.112 | c-$C_6H_{11}$ | 2-Cl(Ph) | H | $CH_3$ | H | H | |
| 1.113 | c-$C_6H_{11}$ | 3-Cl(Ph) | H | $CH_3$ | H | H | |
| 1.114 | c-$C_6H_{11}$ | 4-Cl(Ph) | H | $CH_3$ | H | H | |
| 1.115 | c-$C_6H_{11}$ | 2,4-Cl(Ph) | H | $CH_3$ | H | H | |
| 1.116 | c-$C_6H_{11}$ | 3,4-Cl(Ph) | H | $CH_3$ | H | H | |
| 1.117 | c-$C_6H_{11}$ | 2-Pyridyl | H | $CH_3$ | H | H | |
| 1.118 | c-$C_6H_{11}$ | 3-Pyridyl | H | $CH_3$ | H | H | |
| 1.119 | c-$C_6H_{11}$ | 4-Pyridyl | H | $CH_3$ | H | H | |
| 1.120 | c-$C_6H_{11}$ | $CH_2$—OPh | H | $CH_3$ | H | H | |
| 1.121 | c-$C_6H_{11}$ | $CH_2$—O-(4-Cl(Ph)) | H | $CH_3$ | H | H | |
| 1.122 | c-$C_6H_{11}$ | $CH_2$—O(4-$CF_3$(Ph)) | H | $CH_3$ | H | H | |
| 1.123 | $CH_3$ | Ph | H | $CH_3$ | $CH_3$ | H | |
| 1.124 | $CH_3$ | 2Cl(Ph) | H | $CH_3$ | *$CH_3$ | H | |
| 1.125 | $CH_3$ | 3Cl(Ph) | H | $CH_3$ | $CH_3$ | H | |
| 1.126 | $CH_3$ | 4Cl(Ph) | H | $CH_3$ | $CH_3$ | H | |
| 1.127 | $CH_3$ | 2,4-Cl(Ph) | H | $CH_3$ | $CH_3$ | H | |
| 1.128 | $CH_3$ | 3,4-Cl(Ph) | H | $CH_3$ | $CH_3$ | H | |
| 1.129 | $CH_3$ | 2-Pyridyl | H | $CH_3$ | $CH_3$ | H | |
| 1.130 | $CH_3$ | 3-#dy1 | H | $CH_3$ | $CH_3$ | H | |
| 1.131 | $CH_3$ | 4-Prrldyl | H | $CH_3$ | $CH_3$ | H | |
| 1.132 | $CH_3$ | $CH_2$—OPh | H | $CH_3$ | $CH_3$ | H | |
| 1.133 | $CH_3$ | $CH_2$—O(2-Cl(Ph)) | H | $CH_3$ | $CH_3$ | H | |
| 1.134 | $CH_3$ | $CH_2$—O(3-Cl(Ph)) | H | $CH_3$ | $CH_3$ | H | |
| 1.135 | $CH_3$ | $CH_2$—O(4-Cl(Ph)) | H | $CH_3$ | $CH_3$ | H | |
| 1.136 | $CH_3$ | $CH_2$—O(2-F(Ph)) | H | $CH_3$ | $CH_3$ | H | |
| 1.137 | $CH_3$ | $CH_2$—O(3-F(Ph)) | H | $CH_3$ | $CH_3$ | H | |
| 1.138 | $CH_3$ | $CH_2$—O(4-F(Ph)) | H | $CH_3$ | $CH_3$ | H | |
| 1.139 | $CH_3$ | $CH_2$—O(2-$CF_3$(Ph)) | H | $CH_3$ | $CH_3$ | H | |
| 1.140 | $CH_3$ | $CH_2$—O(3-$CF_3$(Ph)) | H | $CH_3$ | $CH_3$ | H | |
| 1.141 | $CH_3$ | $CH_2$—O(4-$CF_3$(Ph)) | H | $CH_3$ | $CH_3$ | H | |
| 1.142 | $C_2H_5$ | Ph | H | $CH_3$ | $CH_3$ | H | |
| 1.143 | $C_2H_5$ | 2-Cl(Ph) | H | $CH_3$ | $CH_3$ | H | |
| 1.144 | $C_2H_5$ | 3-Cl(Ph) | H | $CH_3$ | $CH_3$ | H | |
| 1.145 | $C_2H_5$ | 4-Cl(Ph) | H | $CH_3$ | $CH_3$ | H | |
| 1.146 | $C_2H_5$ | 2,4-Cl(Ph) | H | $CH_3$ | $CH_3$ | H | |
| 1.147 | $C_2H_5$ | 3,4-Cl(Ph) | H | $CH_3$ | $CH_3$ | H | |
| 1.148 | $C_2H_5$ | 2-Pyridyl | H | $CH_3$ | $CH_3$ | H | |
| 1.149 | $C_2H_5$ | 3-Pyridyl | H | $CH_3$ | $CH_3$ | H | |
| 1.150 | $C_2H_5$ | 4-Pyridyl | H | $CH_3$ | $CH_3$ | H | |
| 1.151 | $C_2H_5$ | $CH_2$—OPh | H | $CH_3$ | $CH_3$ | H | |
| 1.152 | $C_2H_5$ | $CH_2$—O-(4-Cl(Ph)) | H | $CH_3$ | $CH_3$ | H | |
| 1.153 | $C_2H_5$ | $CH_2$—O(4-$CF_3$(Ph)) | H | $CH_3$ | $CH_3$ | H | |
| 1.154 | iso-$C_3H_7$ | Ph | H | $CH_3$ | $CH_3$ | H | |
| 1.155 | iso-$C_3H_7$ | 2-Cl(Ph) | H | $CH_3$ | $CH_3$ | H | |
| 1.156 | iso-$C_3H_7$ | 3-Cl(Ph) | H | $CH_3$ | $CH_3$ | H | |
| 1.157 | iso-$C_3H_7$ | 4-Cl(Ph) | H | $CH_3$ | $CH_3$ | H | |
| 1.158 | iso-$C_3H_7$ | 2,4-Cl(Ph) | H | $CH_3$ | $CH_3$ | H | |
| 1.159 | iso-$C_3H_7$ | 3,4-Cl(Ph) | H | $CH_3$ | $CH_3$ | H | |
| 1.160 | iso-$C_3H_7$ | $CH_2$—OPh | H | $CH_3$ | $CH_3$ | H | |
| 1.161 | iso-$C_3H_7$ | 2-Pyridyl | H | $CH_3$ | $CH_3$ | H | |
| 1.162 | iso-$C_3H_7$ | 3-Pyridyl | H | $CH_3$ | $CH_3$ | H | |
| 1.163 | iso-$C_3H_7$ | 4-Pyridyl | H | $CH_3$ | $CH_3$ | H | |
| 1.164 | iso-$C_3H_7$ | $CH_2$—O-(4-Cl(Ph)) | H | $CH_3$ | $CH_3$ | H | |
| 1.165 | iso-$C_3H_7$ | $CH_2$—O(4-$CF_3$(Ph)) | H | $CH_3$ | $CH_3$ | H | |
| 1.166 | c-$C_6H_{11}$ | Ph | H | $CH_3$ | $CH_3$ | H | |
| 1.167 | c-$C_6H_{11}$ | 2Cl(Ph) | H | $CH_3$ | $CH_3$ | H | |
| 1.168 | c-$C_6H_{11}$ | 3Cl(Ph) | H | $CH_3$ | $CH_3$ | H | |
| 1.169 | c-$C_6H_{11}$ | 4Cl(Ph) | H | $CH_3$ | $CH_3$ | H | |
| 1.170 | c-$C_6H_{11}$ | 2,4-Cl(Ph) | H | $CH_3$ | $CH_3$ | H | |
| 1.171 | c-$C_6H_{11}$ | 3,4-Cl(Ph) | H | $CH_3$ | $CH_3$ | H | |
| 1.172 | c-$C_6H_{11}$ | $CH_2$—OPh | H | $CH_3$ | $CH_3$ | H | |
| 1.173 | c-$C_6H_{11}$ | 2-Pyridyl | H | $CH_3$ | $CH_3$ | H | |
| 1.174 | c-$C_6H_{11}$ | 3-Pyridyl | H | $CH_3$ | $CH_3$ | H | |
| 1.175 | c-$C_6H_{11}$ | 4-Pyridyl | H | $CH_3$ | $CH_3$ | H | |
| 1.176 | c-$C_6H_{11}$ | $CH_2$—O-(4-Cl(Ph)) | H | $CH_3$ | $CH_3$ | H | |
| 1.177 | c-$C_6H_{11}$ | $CH_2$—O(4-$CF_3$(Ph)) | H | $CH_3$ | $CH_3$ | H | |
| 1.178 | $CH_3$ | Ph | H | $CH_3$ | $CH_3$ | $CH_3$ | |
| 1.179 | $CH_3$ | 2-Cl(Ph) | H | $CH_3$ | $CH_3$ | $CH_3$ | |
| 1.180 | $CH_3$ | 3-Cl(Ph) | H | $CH_3$ | $CH_3$ | $CH_3$ | |
| 1.181 | $CH_3$ | 4-Cl(Ph) | H | $CH_3$ | $CH_3$ | $CH_3$ | |
| 1.182 | $CH_3$ | 2,4-Cl(Ph) | H | $CH_3$ | $CH_3$ | $CH_3$ | |
| 1.183 | $CH_3$ | 3,4-Cl(Ph) | H | $CH_3$ | $CH_3$ | $CH_3$ | |
| 1.184 | $CH_3$ | 2-Pyridyl | H | $CH_3$ | $CH_3$ | $CH_3$ | |
| 1.185 | $CH_3$ | 3-Pyridyl | H | $CH_3$ | $CH_3$ | $CH_3$ | |
| 1.186 | $CH_3$ | 4-Pyridyl | H | $CH_3$ | $CH_3$ | $CH_3$ | |

TABLE I-continued

| Cmpd # | R | $R_4$ | $R_5$ | $R_6$ | $R_7$ | $R_8$ | Physical Property |
|---|---|---|---|---|---|---|---|
| 1.187 | $CH_3$ | $CH_2$—OPh | H | $CH_3$ | $CH_3$ | $CH_3$ | |
| 1.188 | $CH_3$ | $CH_2$—O(2-Cl(Ph)) | H | $CH_3$ | $CH_3$ | $CH_3$ | |
| 1.189 | $CH_3$ | $CH_2$—O(3-Cl(Ph)) | H | $CH_3$ | $CH_3$ | $CH_3$ | |
| 1.190 | $CH_3$ | $CH_2$—O(4-Cl(Ph)) | H | $CH_3$ | $CH_3$ | $CH_3$ | |
| 1.191 | $CH_3$ | $CH_2$—O(2-F(Ph)) | H | $CH_3$ | $CH_3$ | $CH_3$ | |
| 1.192 | $CH_3$ | $CH_2$—O(3-F(Ph)) | H | $CH_3$ | $CH_3$ | $CH_3$ | |
| 1.193 | $CH_3$ | $CH_2$—O(4-F(Ph)) | H | $CH_3$ | $CH_3$ | $CH_3$ | |
| 1.194 | $CH_3$ | $CH_2$—O(2-$CF_3$(Ph)) | H | $CH_3$ | $CH_3$ | $CH_3$ | |
| 1.195 | $CH_3$ | $CH_2$—O(3-$CF_3$(Ph)) | H | $CH_3$ | $CH_3$ | $CH_3$ | |
| 1.196 | $CH_3$ | $CH_2$—O(4-$CF_3$(Ph)) | H | $CH_3$ | $CH_3$ | $CH_3$ | |
| 1.197 | $C_2H_5$ | Ph | H | $CH_3$ | $CH_3$ | $CH_3$ | |
| 1.198 | $C_2H_5$ | 2-Cl(Ph) | H | $CH_3$ | $CH_3$ | $CH_3$ | |
| 1.199 | $C_2H_5$ | 3-Cl(Ph) | H | $CH_3$ | $CH_3$ | $CH_3$ | |
| 1.200 | $C_2H_5$ | 4-Cl(Ph) | H | $CH_3$ | $CH_3$ | $CH_3$ | |
| 1.201 | $C_2H_5$ | 2,4-Cl(Ph) | H | $CH_3$ | $CH_3$ | $CH_3$ | |
| 1.202 | $C_2H_5$ | 3,4-Cl(Ph) | H | $CH_3$ | $CH_3$ | $CH_3$ | |
| 1.203 | $C_2H_5$ | 2-Pyridyl | H | $CH_3$ | $CH_3$ | $CH_3$ | |
| 1.204 | $C_2H_5$ | 3-Pyridyl | H | $CH_3$ | $CH_3$ | $CH_3$ | |
| 1.205 | $C_2H_5$ | 4-Pyridyl | H | $CH_3$ | $CH_3$ | $CH_3$ | |
| 1.206 | $C_2H_5$ | $CH_2$—OPh | H | $CH_3$ | $CH_3$ | $CH_3$ | |
| 1.207 | $C_2H_5$ | $CH_2$—O(4-Cl(Ph)) | H | $CH_3$ | $CH_3$ | $CH_3$ | |
| 1.208 | $C_2H_5$ | $CH_2$—O(4-$CF_3$(Ph)) | H | $CH_3$ | $CH_3$ | $CH_3$ | |
| 1.209 | iso-$C_3H_7$ | Ph | H | $CH_3$ | $CH_3$ | $CH_3$ | |
| 1.210 | iso-$C_3H_7$ | 2-Cl(Ph) | H | $CH_3$ | $CH_3$ | $CH_3$ | |
| 1.211 | iso-$C_3H_7$ | 3-Cl(Ph) | H | $CH_3$ | $CH_3$ | $CH_3$ | |
| 1.212 | iso-$C_3H_7$ | 4-Cl(Ph) | H | $CH_3$ | $CH_3$ | $CH_3$ | |
| 1.213 | iso-$C_3H_7$ | 2,4-Cl(Ph) | H | $CH_3$ | $CH_3$ | $CH_3$ | |
| 1.214 | iso-$C_3H_7$ | 3,4-Cl(Ph) | H | $CH_3$ | $CH_3$ | $CH_3$ | |
| 1.215 | iso-$C_3H_7$ | $CH_2$—OPh | H | $CH_3$ | $CH_3$ | $CH_3$ | |
| 1.216 | iso-$C_3H_7$ | 2-Pyridyl | H | $CH_3$ | $CH_3$ | $CH_3$ | |
| 1.217 | iso-$C_3H_7$ | 3-Pyridyl | H | $CH_3$ | $CH_3$ | $CH_3$ | |
| 1.218 | iso-$C_3H_7$ | 4-Pyridyl | H | $CH_3$ | $CH_3$ | $CH_3$ | |
| 1.219 | iso-$C_3H_7$ | $CH_2$—O(4-Cl(Ph)) | H | $CH_3$ | $CH_3$ | $CH_3$ | |
| 1.220 | iso-$C_3H_7$ | $CH_2$—O(4-$CF_3$(Ph)) | H | $CH_3$ | $CH_3$ | $CH_3$ | |
| 1.221 | c-$C_6H_{11}$ | Ph | H | $CH_3$ | $CH_3$ | $CH_3$ | |
| 1.222 | c-$C_6H_{11}$ | 2-Cl(Ph) | H | $CH_3$ | $CH_3$ | $CH_3$ | |
| 1.223 | c-$C_6H_{11}$ | 3-Cl(Ph) | H | $CH_3$ | $CH_3$ | $CH_3$ | |
| 1.224 | c-$C_6H_{11}$ | 4-Cl(Ph) | H | $CH_3$ | $CH_3$ | $CH_3$ | |
| 1.225 | c-$C_6H_{11}$ | 2,4-Cl(Ph) | H | $CH_3$ | $CH_3$ | $CH_3$ | |
| 1.226 | c-$C_6H_{11}$ | 3,4-Cl(Ph) | H | $CH_3$ | $CH_3$ | $CH_3$ | |
| 1.227 | c-$C_6H_{11}$ | $CH_2$—OPh | H | $CH_3$ | $CH_3$ | $CH_3$ | |
| 1.228 | c-$C_6H_{11}$ | 2-Pyridyl | H | $CH_3$ | $CH_3$ | $CH_3$ | |
| 1.229 | c-$C_6H_{11}$ | 3-Pyridyl | H | $CH_3$ | $CH_3$ | $CH_3$ | |
| 1.230 | c-$C_6H_{11}$ | 4-Pyridyl | H | $CH_3$ | $CH_3$ | $CH_3$ | |
| 1.231 | c-$C_6H_{11}$ | $CH_2$—O(4-Cl(Ph)) | H | $CH_3$ | $CH_3$ | $CH_3$ | |
| 1.232 | c-$C_6H_{11}$ | $CH_2$—O(4-$CF_3$(Ph)) | H | $CH_3$ | $CH_3$ | $CH_3$ | |
| 1.233 | $CH_3$ | CN | H | H | H | H | |
| 1.234 | $CH_3$ | $CO_2CH_3$ | H | H | H | H | |
| 1.235 | $CH_3$ | CN | H | $CH_3$ | H | H | |
| 1.236 | $CH_3$ | $CO_2CH_3$ | H | $CH_3$ | H | H | |
| 1.237 | $CH_3$ | CN | H | $CH_3$ | $CH_3$ | H | |
| 1.238 | $CH_3$ | $CO_2CH_3$ | H | $CH_3$ | $CH_3$ | H | |
| 1.239 | $C_2H_5$ | CN | H | H | H | H | |
| 1.240 | $C_2H_5$ | $CO_2CH_3$ | H | H | H | H | |
| 1.241 | $C_2H_5$ | CN | H | $CH_3$ | H | H | |
| 1.242 | $C_2H_5$ | $CO_2CH_3$ | H | $CH_3$ | H | H | |
| 1.243 | $C_2H_5$ | CN | H | $CH_3$ | $CH_3$ | H | |
| 1.244 | $C_2H_5$ | $CO_2CH_3$ | H | $CH_3$ | $CH_3$ | H | |
| 1.245 | iso-$C_3H_7$ | CN | H | H | H | H | |
| 1.246 | iso-$C_3H_7$ | $CO_2CH_3$ | H | H | H | H | |
| 1.247 | iso-$C_3H_7$ | CN | H | $CH_3$ | H | H | |
| 1.248 | iso-$C_3H_7$ | $CO_2CH_3$ | H | $CH_3$ | H | H | |
| 1.249 | iso-$C_3H_7$ | CN | H | $CH_3$ | $CH_3$ | H | |
| 1.250 | iso-$C_3H_7$ | $CO_2CH_3$ | H | $CH_3$ | $CH_3$ | H | |
| 1.251 | c-$C_6H_{11}$ | CN | H | $CH_3$ | $CH_3$ | H | |
| 1.252 | c-$C_6H_{11}$ | $CO_2CH_3$ | H | $CH_3$ | $CH_3$ | H | |
| 1.253 | $CH_3$ | CN | H | $CH_3$ | $CH_3$ | $CH_3$ | |
| 1.254 | $CH_3$ | $CO_2CH_3$ | H | $CH_3$ | $CH_3$ | $CH_3$ | |
| 1.255 | $C_2H_5$ | CN | H | $CH_3$ | $CH_3$ | $CH_3$ | |
| 1.256 | $C_2H_5$ | $CO_2CH_3$ | H | $CH_3$ | $CH_3$ | $CH_3$ | |
| 1.257 | iso-$C_3H_7$ | CN | H | $CH_3$ | $CH_3$ | $CH_3$ | |
| 1.258 | iso-$C_3H_7$ | $CO_2CH_3$ | H | $CH_3$ | $CH_3$ | $CH_3$ | |
| 1.259 | c-$C_6H_{11}$ | CN | H | $CH_3$ | $CH_3$ | $CH_3$ | |
| 1.260 | c-$C_6H_{11}$ | $CO_2CH_3$ | H | $CH_3$ | $CH_3$ | $CH_3$ | |

Typical compounds encompassed by the present invention of Formula I include those compounds presented in Table 2 of Formula III wherein X is nitrogen, $R_2$ and $R_3$ are hydrogen, $R_1$ is $C(R_6R_7R_8)$ wherein $R_6$, $R_7$, and $R_8$ are defined in Table 2.

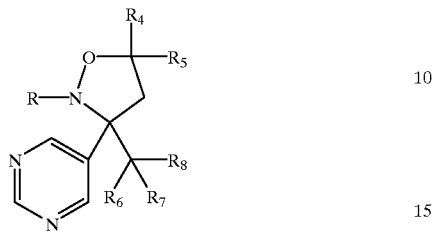

(III)

TABLE 2

| Cmpd # | R | $R_4$ | $R_5$ | $R_6$ | $R_7$ | $R_8$ | Physical Property |
|---|---|---|---|---|---|---|---|
| 2.1 | $CH_3$ | Ph | H | H | H | H | |
| 2.2 | $CH_3$ | 2-Cl(Ph) | H | H | H | H | |
| 2.3 | $CH_3$ | 3-Cl(Ph) | H | H | H | H | |
| 2.4 | $CH_3$ | 4-Cl(Ph) | H | H | H | H | |
| 2.5 | $CH_3$ | 2-F(Ph) | H | H | H | H | |
| 2.6 | $CH_3$ | 3-F(Ph) | H | H | H | H | |
| 2.7 | $CH_3$ | 4-F(Ph) | H | H | H | H | |
| 2.8 | $CH_3$ | 2-Br(Ph) | H | H | H | H | |
| 2.9 | $CH_3$ | 3-Br(Ph) | H | H | H | H | |
| 2.10 | $CH_3$ | 4-Br(Ph) | H | H | H | H | |
| 2.11 | $CH_3$ | 2-$CF_3$(Ph) | H | H | H | H | |
| 2.12 | $CH_3$ | 3-$CF_3$(Ph) | H | H | H | H | |
| 2.13 | $CH_3$ | 4-$CF_3$(Ph) | H | H | H | H | |
| 2.14 | $CH_3$ | 2-$CH_3$(Ph) | H | H | H | H | |
| 2.15 | $CH_3$ | 3-$CH_3$(Ph) | H | H | H | H | |
| 2.16 | $CH_3$ | 4-$CH_3$(Ph) | H | H | H | H | |
| 2.17 | $CH_3$ | 2-$OCH_3$(Ph) | H | H | H | H | |
| 2.18 | $CH_3$ | 3-$OCH_3$(Ph) | H | H | H | H | |
| 2.19 | $CH_3$ | 4-$OCH_3$(Ph) | H | H | H | H | |
| 2.20 | $CH_3$ | 1-Naphthyl | H | H | H | H | |
| 2.21 | $CH_3$ | 2-Naphthyl | H | H | H | H | |
| 2.22 | $CH_3$ | 2,4-Cl(Ph) | H | H | H | H | |
| 2.23 | $CH_3$ | 3,4-Cl(Ph) | H | H | H | H | |
| 2.24 | $CH_3$ | 3,5-Cl(Ph) | H | H | H | H | |
| 2.25 | $CH_3$ | 2-Pyridyl | H | H | H | H | |
| 2.26 | $CH_3$ | 3-Pyridyl | H | H | H | H | |
| 2.27 | $CH_3$ | 4-Pyridyl | H | H | H | H | |
| 2.28 | $CH_3$ | $CH_2$—O(Ph) | H | H | H | H | |
| 2.29 | $CH_3$ | $CH_2$—O(2-Cl(Ph)) | H | H | H | H | |
| 2.30 | $CH_3$ | $CH_2$—O(3-Cl(Ph)) | H | H | H | H | |
| 2.31 | $CH_3$ | $CH_2$—O(4-Cl(Ph)) | H | H | H | H | |
| 2.32 | $CH_3$ | $CH_2$—O(2-F(Ph)) | H | H | H | H | |
| 2.33 | $CH_3$ | $CH_2$—O(3-F(Ph)) | H | H | H | H | |
| 2.34 | $CH_3$ | $CH_2$—O(4-F(Ph)) | H | H | H | H | |
| 2.35 | $CH_3$ | $CH_2$—O(3-$CF_3$(Ph)) | H | H | H | H | |
| 2.36 | $CH_3$ | $CH_2$—O(4-$CF_3$(Ph)) | H | H | H | H | |
| 2.37 | $C_2H_5$ | Ph | H | H | H | H | |
| 2.38 | $C_2H_5$ | 2-Cl(Ph) | H | H | H | H | |
| 2.39 | $C_2H_5$ | 3-Cl(Ph) | H | H | H | H | |
| 2.40 | $C_2H_5$ | 4-Cl(Ph) | H | H | H | H | |
| 2.41 | $C_2H_5$ | 2,4-Cl(Ph) | H | H | H | H | |
| 2.42 | $C_2H_5$ | 3,4-Cl(Ph) | H | H | H | H | |
| 2.43 | $C_2H_5$ | 2-Pyridyl | H | H | H | H | |
| 2.44 | $C_2H_5$ | 3-Pyridyl | H | H | H | H | |
| 2.45 | $C_2H_5$ | 4-Pyridyl | H | H | H | H | |
| 2.46 | $C_2H_5$ | $CH_2$—OPh | H | H | H | H | |
| 2.47 | $C_2H_5$ | $CH_2$—O(4-Cl(Ph)) | H | H | H | H | |
| 2.48 | $C_2H_5$ | $CH_2$—O(4-$CF_3$(Ph)) | H | H | H | H | |
| 2.49 | iso-$C_3H_7$ | Ph | H | H | H | H | |
| 2.5 | iso-$C_3H_7$ | 2-Cl(Ph) | H | H | H | H | |
| 2.51 | iso-$C_3H_7$ | 3-Cl(Ph) | H | H | H | H | |
| 2.52 | iso-$C_3H_7$ | 4-Cl(Ph) | H | H | H | H | |
| 2.53 | iso-$C_3H_7$ | 2,4-Cl(Ph) | H | H | H | H | |
| 2.54 | iso-$C_3H_7$ | 3,4-Cl(Ph) | H | H | H | H | |
| 2.55 | iso-$C_3H_7$ | 2-Pyridyl | H | H | H | H | |

TABLE 2-continued

| Cmpd # | R | R$_4$ | R$_5$ | R$_6$ | R$_7$ | R$_8$ | Physical Property |
|---|---|---|---|---|---|---|---|
| 2.56 | iso-C$_3$H$_7$ | 3-Pyridyl | H | H | H | H | |
| 2.57 | iso-C$_3$H$_7$ | 4-Pyridyl | H | H | H | H | |
| 2.58 | iso-C$_3$H$_7$ | CH$_2$—OPh | H | H | H | H | |
| 2.59 | iso-C$_3$H$_7$ | CH$_2$—O(4-Cl(Ph)) | H | H | H | H | |
| 2.60 | iso-C$_3$H$_7$ | CH$_2$—O(4-CF$_3$(Ph)) | H | H | H | H | |
| 2.61 | c-C$_6$H$_{11}$ | Ph | H | H | H | H | |
| 2.62 | c-C$_6$H$_{11}$ | 2Cl(Ph) | H | H | H | H | |
| 2.63 | c-C$_6$H$_{11}$ | 3Cl(Ph) | H | H | H | H | |
| 2.64 | c-C$_6$H$_{11}$ | 4Cl(Ph) | H | H | H | H | |
| 2.65 | c-C$_6$H$_{11}$ | 2,4-Cl(Ph) | H | H | H | H | |
| 2.66 | c-C$_6$H$_{11}$ | 3,4-Cl(Ph) | H | H | H | H | |
| 2.67 | c-C$_6$H$_{11}$ | 2-Pyridyl | H | H | H | H | |
| 2.68 | c-C$_6$H$_{11}$ | 3-Pyridyl | H | H | H | H | |
| 2.69 | c-C$_6$H$_{11}$ | 4-Pyridyl | H | H | H | H | |
| 2.70 | c-C$_6$H$_{11}$ | CH$_2$—OPh | H | H | H | H | |
| 2.71 | c-C$_6$H$_{11}$ | CH$_2$—O(4-Cl(Ph)) | H | H | H | H | |
| 2.72 | c-C$_6$H$_{11}$ | CH$_2$—O(4-CF$_3$(Ph)) | H | H | H | H | |
| 2.73 | CH$_3$ | Ph | H | CH$_3$ | H | H | |
| 2.74 | CH$_3$ | 2-Cl(Ph) | H | CH$_3$ | H | H | |
| 2.75 | CH$_3$ | 3-Cl(Ph) | H | CH$_3$ | H | H | |
| 2.76 | CH$_3$ | 4-Cl(Ph) | H | CH$_3$ | H | H | |
| 2.77 | CH$_3$ | 2,4-Cl(Ph) | H | CH$_3$ | H | H | |
| 2.78 | CH$_3$ | 3,4-Cl(Ph) | H | CH$_3$ | H | H | |
| 2.79 | CH$_3$ | 2-Pyridyl | H | CH$_3$ | H | H | |
| 2.80 | CH$_3$ | 3-Pyridyl | H | CH$_3$ | H | H | |
| 2.81 | CH$_3$ | 4-Pyridyl | H | CH$_3$ | H | H | |
| 2.82 | CH$_3$ | CH$_2$—OPh | H | CH$_3$ | H | H | |
| 2.83 | CH$_3$ | CH$_2$—O(2-Cl(Ph)) | H | CH$_3$ | H | H | |
| 2.84 | CH$_3$ | CH$_2$—O(3-Cl(Ph)) | H | CH$_3$ | H | H | |
| 2.85 | CH$_3$ | CH$_2$—O(4-Cl(Ph)) | H | CH$_3$ | H | H | |
| 2.86 | CH$_3$ | CH$_2$—O(2-F(Ph)) | H | CH$_3$ | H | H | |
| 2.87 | CH$_3$ | CH$_2$—O(3-F(Ph)) | H | CH$_3$ | H | H | |
| 2.88 | CH$_3$ | CH$_2$—O(4-F(Ph)) | H | CH$_3$ | H | H | |
| 2.89 | CH$_3$ | CH$_2$—O(2-CF$_3$(Ph)) | H | CH$_3$ | H | H | |
| 2.90 | CH$_3$ | CH$_2$—O(3-CF$_3$(Ph)) | H | CH$_3$ | H | H | |
| 2.91 | CH$_3$ | CH$_2$—O(4-CF$_3$(Ph)) | H | CH$_3$ | H | H | |
| 2.92 | C$_2$H$_5$ | Ph | H | CH$_3$ | H | H | |
| 2.93 | C$_2$H$_5$ | 2-Cl(Ph) | H | CH$_3$ | H | H | |
| 2.94 | C$_2$H$_5$ | 3-Cl(Ph) | H | CH$_3$ | H | H | |
| 2.95 | C$_2$H$_5$ | 4-Cl(Ph) | H | CH$_3$ | H | H | |
| 2.96 | C$_2$H$_5$ | 2,4-Cl(Ph) | H | CH$_3$ | H | H | |
| 2.97 | C$_2$H$_5$ | 3,4-Cl(Ph) | H | CH$_3$ | H | H | |
| 2.98 | C$_2$H$_5$ | 2-Pyridyl | H | CH$_3$ | H | H | |
| 2.99 | C$_2$H$_5$ | 3-Pyridyl | H | CH$_3$ | H | H | |
| 2.100 | C$_2$H$_5$ | 4-Pyridyl | H | CH$_3$ | H | H | |
| 2.101 | C$_2$H$_5$ | CH$_2$—OPh | H | CH$_3$ | H | H | |
| 2.102 | C$_2$H$_5$ | CH$_2$—O(4-Cl(Ph)) | H | CH$_3$ | H | H | |
| 2.103 | C$_2$H$_5$ | CH$_2$—O(4-CF$_3$(Ph)) | H | CH$_3$ | H | H | |
| 2.104 | iso-C$_3$H$_7$ | Ph | H | CH$_3$ | H | H | |
| 2.105 | iso-C$_3$H$_7$ | 2-Cl(Ph) | H | CH$_3$ | H | H | |
| 2.106 | iso-C$_3$H$_7$ | 3-Cl(Ph) | H | CH$_3$ | H | H | |
| 2.107 | iso-C$_3$H$_7$ | 4-Cl(Ph) | H | CH$_3$ | H | H | |
| 2.108 | iso-C$_3$H$_7$ | 2,4-Cl(Ph) | H | CH$_3$ | H | H | |
| 2.109 | iso-C$_3$H$_7$ | 3,4-Cl(Ph) | H | CH$_3$ | H | H | |
| 2.110 | iso-C$_3$H$_7$ | 2-Pyridyl | H | CH$_3$ | H | H | |
| 2.111 | iso-C$_3$H$_7$ | 3-Pyridyl | H | CH$_3$ | H | H | |
| 2.112 | iso-C$_3$H$_7$ | 4-Pyridyl | H | CH$_3$ | H | H | |
| 2.113 | iso-C$_3$H$_7$ | CH$_2$—OPh | H | CH$_3$ | H | H | |
| 2.114 | iso-C$_3$H$_7$ | CH$_2$—O(4-Cl(Ph)) | H | CH$_3$ | H | H | |
| 2.115 | iso-C$_3$H$_7$ | CH$_2$—O(4-CF$_3$(Ph)) | H | CH$_3$ | H | H | |
| 2.116 | c-C$_6$H$_{11}$ | Ph | H | CH$_3$ | H | H | |
| 2.117 | c-C$_6$H$_{11}$ | 2-Cl(Ph) | H | CH$_3$ | H | H | |
| 2.118 | c-C$_6$H$_{11}$ | 3-Cl(Ph) | H | CH$_3$ | H | H | |
| 2.119 | c-C$_6$H$_{11}$ | 4-Cl(Ph) | H | CH$_3$ | H | H | |
| 2.120 | c-C$_6$H$_{11}$ | 2,4-Cl(Ph) | H | CH$_3$ | H | H | |
| 2.121 | c-C$_6$H$_{11}$ | 3,4-Cl(Ph) | H | CH$_3$ | H | H | |
| 2.122 | c-C$_6$H$_{11}$ | CH$_2$—O-Ph | H | CH$_3$ | H | H | |
| 2.123 | c-C$_6$H$_{11}$ | 2-Pyridyl | H | CH$_3$ | H | H | |
| 2.124 | c-C$_6$H$_{11}$ | 3-Pyridyl | H | CH$_3$ | H | H | |
| 2.125 | c-C$_6$H$_{11}$ | 4-Pyridyl | H | CH$_3$ | H | H | |
| 2.126 | c-C$_6$H$_{11}$ | CH$_2$—O(4-Cl(Ph)) | H | CH$_3$ | H | H | |
| 2.127 | c-C$_6$H$_{11}$ | CH$_2$—O(4-CF$_3$(Ph)) | H | CH$_3$ | H | H | |
| 2.128 | CH$_3$ | Ph | H | CH$_3$ | CH$_3$ | H | |
| 2.129 | CH$_3$ | 2-Cl(Ph) | H | CH$_3$ | CH$_3$ | H | |
| 2.130 | CH$_3$ | 3-Cl(Ph) | H | CH$_3$ | CH$_3$ | H | |
| 2.131 | CH$_3$ | 4-Cl(Ph) | H | CH$_3$ | CH$_3$ | H | |
| 2.132 | CH$_3$ | 2,4-Cl(Ph) | H | CH$_3$ | CH$_3$ | H | |

TABLE 2-continued

| Cmpd # | R | R$_4$ | R$_5$ | R$_6$ | R$_7$ | R$_8$ | Physical Property |
|---|---|---|---|---|---|---|---|
| 2.133 | CH$_3$ | 3,4-Cl(Ph) | H | CH$_3$ | CH$_3$ | H | |
| 2.134 | CH$_3$ | 2-Pyridyl | H | CH$_3$ | CH$_3$ | H | |
| 2.135 | CH$_3$ | 3-Pyridyl | H | CH$_3$ | CH$_3$ | H | |
| 2.136 | CH$_3$ | 4-Pyridyl | H | CH$_3$ | CH$_3$ | H | |
| 2.137 | CH$_3$ | CH$_2$—OPh | H | CH$_3$ | CH$_3$ | H | |
| 2.138 | CH$_3$ | CH$_2$—O(2-Cl(Ph)) | H | CH$_3$ | CH$_3$ | H | |
| 2.139 | CH$_3$ | CH$_2$—O(3-Cl(Ph)) | H | CH$_3$ | CH$_3$ | H | |
| 2.140 | CH$_3$ | CH$_2$—O(4-Cl(Ph)) | H | CH$_3$ | CH$_3$ | H | |
| 2.141 | CH$_3$ | CH$_2$—O(2-F(Ph)) | H | CH$_3$ | CH$_3$ | H | |
| 2.142 | CH$_3$ | CH$_2$—O(3-F(Ph)) | H | CH$_3$ | CH$_3$ | H | |
| 2.143 | CH$_3$ | CH$_2$—O(4-F(Ph)) | H | CH$_3$ | CH$_3$ | H | |
| 2.144 | CH$_3$ | CH$_2$—O(2-CF$_3$(Ph)) | H | CH$_3$ | CH$_3$ | H | |
| 2.145 | CH$_3$ | CH$_2$—O(3-CF$_3$(Ph)) | H | CH$_3$ | CH$_3$ | H | |
| 2.146 | CH$_3$ | CH$_2$—O(4-CF$_3$(Ph)) | H | CH$_3$ | CH$_3$ | H | |
| 2.147 | C$_2$H$_5$ | Ph | H | CH$_3$ | CH$_3$ | H | |
| 2.148 | C$_2$H$_5$ | 2-Cl(Ph) | H | CH$_3$ | CH$_3$ | H | |
| 2.149 | C$_2$H$_5$ | 3-Cl(Ph) | H | CH$_3$ | CH$_3$ | H | |
| 2.150 | C$_2$H$_5$ | 4-Cl(Ph) | H | CH$_3$ | CH$_3$ | H | |
| 2.151 | C$_2$H$_5$ | 2,4-Cl(Ph) | H | CH$_3$ | CH$_3$ | H | |
| 2.152 | C$_2$H$_5$ | 3,4-Cl(Ph) | H | CH$_3$ | CH$_3$ | H | |
| 2.153 | C$_2$H$_5$ | 2-Pyridyl | H | CH$_3$ | CH$_3$ | H | |
| 2.154 | C$_2$H$_5$ | 3-Pyridyl | H | CH$_3$ | CH$_3$ | H | |
| 2.155 | C$_2$H$_5$ | 4-Pyridyl | H | CH$_3$ | CH$_3$ | H | |
| 2.156 | C$_2$H$_5$ | CH$_2$—OPh | H | CH$_3$ | CH$_3$ | H | |
| 2.157 | C$_2$H$_5$ | CH$_2$—O(4-Cl(Ph)) | H | CH$_3$ | CH$_3$ | H | |
| 2.158 | C$_2$H$_5$ | CH$_2$—O(4-CF$_3$(Ph)) | H | CH$_3$ | CH$_3$ | H | |
| 2.159 | iso-C$_3$H$_7$ | Ph | H | CH$_3$ | CH$_3$ | H | |
| 2.160 | iso-C$_3$H$_7$ | 2-Cl(Ph) | H | CH$_3$ | CH$_3$ | H | |
| 2.161 | iso-C$_3$H$_7$ | 3-Cl(Ph) | H | CH$_3$ | CH$_3$ | H | |
| 2.162 | iso-C$_3$H$_7$ | 4-Cl(Ph) | H | CH$_3$ | CH$_3$ | H | |
| 2.163 | iso-C$_3$H$_7$ | 2,4-Cl(Ph) | H | CH$_3$ | CH$_3$ | H | |
| 2.164 | iso-C$_3$H$_7$ | 3,4-Cl(Ph) | H | CH$_3$ | CH$_3$ | H | |
| 2.165 | iso-C$_3$H$_7$ | 2-Pyridyl | H | CH$_3$ | CH$_3$ | H | |
| 2.166 | iso-C$_3$H$_7$ | 3-Pyridyl | H | CH$_3$ | CH$_3$ | H | |
| 2.167 | iso-C$_3$H$_7$ | 4-Pyridyl | H | CH$_3$ | CH$_3$ | H | |
| 2.168 | iso-C$_3$H$_7$ | CH$_2$—OPh | H | CH$_3$ | CH$_3$ | H | |
| 2.169 | iso-C$_3$H$_7$ | CH$_2$—O(4-Cl(Ph)) | H | CH$_3$ | CH$_3$ | H | |
| 2.170 | iso-C$_3$H$_7$ | CH$_2$—O(4-CF$_3$(Ph)) | H | CH$_3$ | CH$_3$ | H | |
| 2.171 | c-C$_6$H$_{11}$ | Ph | H | CH$_3$ | CH$_3$ | H | |
| 2.172 | c-C$_6$H$_{11}$ | 2-Cl(Ph) | H | CH$_3$ | CH$_3$ | H | |
| 2.173 | c-C$_6$H$_{11}$ | 3-Cl(Ph) | H | CH$_3$ | CH$_3$ | H | |
| 2.174 | c-C$_6$H$_{11}$ | 4-Cl(Ph) | H | CH$_3$ | CH$_3$ | H | |
| 2.175 | c-C$_6$H$_{11}$ | 2,4-Cl(Ph) | H | CH$_3$ | CH$_3$ | H | |
| 2.176 | c-C$_6$H$_{11}$ | 3,4-Cl(Ph) | H | CH$_3$ | CH$_3$ | H | |
| 2.177 | c-C$_6$H$_{11}$ | 2-Pyridyl | H | CH$_3$ | CH$_3$ | H | |
| 2.178 | c-C$_6$H$_{11}$ | 3-Pyridyl | H | CH$_3$ | CH$_3$ | H | |
| 2.179 | c-C$_6$H$_{11}$ | 4-Pyridyl | H | CH$_3$ | CH$_3$ | H | |
| 2.180 | c-C$_6$H$_{11}$ | CH$_2$—OPh | H | CH$_3$ | CH$_3$ | H | |
| 2.181 | c-C$_6$H$_{11}$ | CH$_2$—O(4-Cl(Ph)) | H | CH$_3$ | CH$_3$ | H | |
| 2.182 | c-C$_6$H$_{11}$ | CH$_2$—O(4-CF$_3$(Ph)) | H | CH$_3$ | CH$_3$ | H | |
| 2.183 | CH$_3$ | Ph | H | CH$_3$ | CH$_3$ | CH$_3$ | |
| 2.184 | CH$_3$ | 2-Cl(Ph) | H | CH$_3$ | CH$_3$ | CH$_3$ | |
| 2.185 | CH$_3$ | 3-Cl(Ph) | H | CH$_3$ | CH$_3$ | CH$_3$ | |
| 2.186 | CH$_3$ | 4-Cl(Ph) | H | CH$_3$ | CH$_3$ | CH$_3$ | |
| 2.187 | CH$_3$ | 2,4-Cl(Ph) | H | CH$_3$ | CH$_3$ | CH$_3$ | |
| 2.188 | CH$_3$ | 3,4-Cl(Ph) | H | CH$_3$ | CH$_3$ | CH$_3$ | |
| 2.189 | CH$_3$ | 2-Pyridyl | H | CH$_3$ | CH$_3$ | CH$_3$ | |
| 2.190 | CH$_3$ | 3-Pyridyl | H | CH$_3$ | CH$_3$ | CH$_3$ | |
| 2.191 | CH$_3$ | 4-Pyridyl | H | CH$_3$ | CH$_3$ | CH$_3$ | |
| 2.192 | CH$_3$ | CH$_2$—OPh | H | CH$_3$ | CH$_3$ | CH$_3$ | |
| 2.193 | CH$_3$ | CH$_2$—O(2-Cl(Ph)) | H | CH$_3$ | CH$_3$ | CH$_3$ | |
| 2.194 | CH$_3$ | CH$_2$—O(3-Cl(Ph)) | H | CH$_3$ | CH$_3$ | CH$_3$ | |
| 2.195 | CH$_3$ | CH$_2$—O(4-Cl(Ph)) | H | CH$_3$ | CH$_3$ | CH$_3$ | |
| 2.196 | CH$_3$ | CH$_2$—O(2-F(Ph)) | H | CH$_3$ | CH$_3$ | CH$_3$ | |
| 2.197 | CH$_3$ | CH$_2$—O(3-F(Ph)) | H | CH$_3$ | CH$_3$ | CH$_3$ | |
| 2.198 | CH$_3$ | CH$_2$—O(4-F(Ph)) | H | CH$_3$ | CH$_3$ | CH$_3$ | |
| 2.199 | CH$_3$ | CH$_2$—O(2-CF$_3$(Ph)) | H | CH$_3$ | CH$_3$ | CH$_3$ | |
| 2.200 | CH$_3$ | CH$_2$—O(3-CF$_3$(Ph)) | H | CH$_3$ | CH$_3$ | CH$_3$ | |
| 2.201 | CH$_3$ | CH$_2$—O(4-CF$_3$(Ph)) | H | CH$_3$ | CH$_3$ | CH$_3$ | |
| 2.202 | C$_2$H$_5$ | Ph | H | CH$_3$ | CH$_3$ | CH$_3$ | |
| 2.203 | C$_2$H$_5$ | 2-Cl(Ph) | H | CH$_3$ | CH$_3$ | CH$_3$ | |
| 2.204 | C$_2$H$_5$ | 3-Cl(Ph) | H | CH$_3$ | CH$_3$ | CH$_3$ | |
| 2.205 | C$_2$H$_5$ | 4-Cl(Ph) | H | CH$_3$ | CH$_3$ | CH$_3$ | |
| 2.206 | C$_2$H$_5$ | 2,4-Cl(Ph) | H | CH$_3$ | CH$_3$ | CH$_3$ | |
| 2.207 | C$_2$H$_5$ | 3,4-Cl(Ph) | H | CH$_3$ | CH$_3$ | CH$_3$ | |
| 2.208 | C$_2$H$_5$ | 2-Pyridyl | H | CH$_3$ | CH$_3$ | CH$_3$ | |
| 2.209 | C$_2$H$_5$ | 3-Pyridyl | H | CH$_3$ | CH$_3$ | CH$_3$ | |

TABLE 2-continued

| Cmpd # | R | $R_4$ | $R_5$ | $R_6$ | $R_7$ | $R_8$ | Physical Property |
|---|---|---|---|---|---|---|---|
| 2.210 | $C_2H_5$ | 4-Pyridyl | H | $CH_3$ | $CH_3$ | $CH_3$ | |
| 2.211 | $C_2H_5$ | $CH_2$—OPh | H | $CH_3$ | $CH_3$ | $CH_3$ | |
| 2.212 | $C_2H_5$ | $CH_2$—O(4-Cl(Ph)) | H | $CH_3$ | $CH_3$ | $CH_3$ | |
| 2.213 | $C_2H_5$ | $CH_2$—O(4-$CF_3$(Ph)) | H | $CH_3$ | $CH_3$ | $CH_3$ | |
| 2.214 | iso-$C_3H_7$ | Ph | H | $CH_3$ | $CH_3$ | $CH_3$ | |
| 2.215 | iso-$C_3H_7$ | 2-Cl(Ph) | H | $CH_3$ | $CH_3$ | $CH_3$ | |
| 2.216 | iso-$C_3H_7$ | 3-Cl(Ph) | H | $CH_3$ | $CH_3$ | $CH_3$ | |
| 2.217 | iso-$C_3H_7$ | 4-Cl(Ph) | H | $CH_3$ | $CH_3$ | $CH_3$ | |
| 2.218 | iso-$C_3H_7$ | 2,4-Cl(Ph) | H | $CH_3$ | $CH_3$ | $CH_3$ | |
| 2.219 | iso-$C_3H_7$ | 3,4-Cl(Ph) | H | $CH_3$ | $CH_3$ | $CH_3$ | |
| 2.220 | iso-$C_3H_7$ | 2-Pyridyl | H | $CH_3$ | $CH_3$ | $CH_3$ | |
| 2.221 | iso-$C_3H_7$ | 3-Pyridyl | H | $CH_3$ | $CH_3$ | $CH_3$ | |
| 2.222 | iso-$C_3H_7$ | 4-Pyridyl | H | $CH_3$ | $CH_3$ | $CH_3$ | |
| 2.223 | iso-$C_3H_7$ | $CH_2$—OPh | H | $CH_3$ | $CH_3$ | $CH_3$ | |
| 2.224 | iso-$C_3H_7$ | $CH_2$—O(4-Cl(Ph)) | H | $CH_3$ | $CH_3$ | $CH_3$ | |
| 2.225 | iso-$C_3H_7$ | $CH_2$—O(4-$CF_3$(Ph)) | H | $CH_3$ | $CH_3$ | $CH_3$ | |
| 2.226 | c-$C_6H_{11}$ | Ph | H | $CH_3$ | $CH_3$ | $CH_3$ | |
| 2.227 | c-$C_6H_{11}$ | 2-Cl(Ph) | H | $CH_3$ | $CH_3$ | $CH_3$ | |
| 2.228 | c-$C_6H_{11}$ | 3-Cl(Ph) | H | $CH_3$ | $CH_3$ | $CH_3$ | |
| 2.229 | c-$C_6H_{11}$ | 4-Cl(Ph) | H | $CH_3$ | $CH_3$ | $CH_3$ | |
| 2.230 | c-$C_6H_{11}$ | 2,4-Cl(Ph) | H | $CH_3$ | $CH_3$ | $CH_3$ | |
| 2.231 | c-$C_6H_{11}$ | 3,4-Cl(Ph) | H | $CH_3$ | $CH_3$ | $CH_3$ | |
| 2.232 | c-$C_6H_{11}$ | 2-Pyridyl | H | $CH_3$ | $CH_3$ | $CH_3$ | |
| 2.233 | c-$C_6H_{11}$ | 3-Pyridyl | H | $CH_3$ | $CH_3$ | $CH_3$ | |
| 2.234 | c-$C_6H_{11}$ | 4-Pyridyl | H | $CH_3$ | $CH_3$ | $CH_3$ | |
| 2.235 | c-$C_6H_{11}$ | $CH_2$—OPh | H | $CH_3$ | $CH_3$ | $CH_3$ | |
| 2.236 | c-$C_6H_{11}$ | $CH_2$—O(4-Cl(Ph)) | H | $CH_3$ | $CH_3$ | $CH_3$ | |
| 2.237 | c-$C_6H_{11}$ | $CH_2$—O(4-$CF_3$(Ph)) | H | $CH_3$ | $CH_3$ | $CH_3$ | |
| 2.238 | $CH_3$ | CN | H | H | H | H | |
| 2.239 | $CH_3$ | $CO_2CH_3$ | H | H | H | H | |
| 2.240 | $CH_3$ | CN | H | $CH_3$ | H | H | |
| 2.241 | $CH_3$ | $CO_2CH_3$ | H | $CH_3$ | H | H | |
| 2.242 | $CH_3$ | CN | H | $CH_3$ | $CH_3$ | H | |
| 2.243 | $CH_3$ | $CO_2CH_3$ | H | $CH_3$ | $CH_3$ | H | |
| 2.244 | $C_2H_5$ | CN | H | H | H | H | |
| 2.245 | $C_2H_5$ | $CO_2CH_3$ | H | H | H | H | |
| 2.246 | $C_2H_5$ | CN | H | $CH_3$ | H | H | |
| 2.247 | $C_2H_5$ | $CO_2CH_3$ | H | $CH_3$ | H | H | |
| 2.248 | $C_2H_5$ | CN | H | $CH_3$ | $CH_3$ | H | |
| 2.249 | $C_2H_5$ | $CO_2CH_3$ | H | $CH_3$ | $CH_3$ | H | |
| 2.250 | iso-$C_3H_7$ | CN | H | H | H | H | |
| 2.251 | iso-$C_3H_7$ | $CO_2CH_3$ | H | H | H | H | |
| 2.252 | iso-$C_3H_7$ | CN | H | $CH_3$ | H | H | |
| 2.253 | iso-$C_3H_7$ | $CO_2CH_3$ | H | $CH_3$ | H | H | |
| 2.254 | iso-$C_3H_7$ | CN | H | $CH_3$ | $CH_3$ | H | |
| 2.255 | iso-$C_3H_7$ | $CO_2CH_3$ | H | $CH_3$ | $CH_3$ | H | |
| 2.256 | c-$C_6H_{11}$ | CN | H | $CH_3$ | $CH_3$ | H | |
| 2.257 | c-$C_6H_{11}$ | $CO_2CH_3$ | H | $CH_3$ | $CH_3$ | H | |
| 2.258 | $CH_3$ | CN | H | $CH_3$ | $CH_3$ | $CH_3$ | |
| 2.259 | $CH_3$ | $CO_2CH_3$ | H | $CH_3$ | $CH_3$ | $CH_3$ | |
| 2.260 | $C_2H_5$ | CN | H | $CH_3$ | $CH_3$ | $CH_3$ | |
| 2.261 | $C_2H_5$ | $CO_2CH_3$ | H | $CH_3$ | $CH_3$ | $CH_3$ | |
| 2.262 | iso-$C_3H_7$ | CN | H | $CH_3$ | $CH_3$ | $CH_3$ | |
| 2.263 | iso-$C_3H_7$ | $CO_2CH_3$ | H | $CH_3$ | $CH_3$ | $CH_3$ | |

Typical compounds encompassed by the present invention of Formula I include those compounds presented in Table 3 of Formula IV, $R_2$, $R_3$, and $R_5$ are hydrogen, and $R_1$, $R_4$, and X are defined in Table 3.

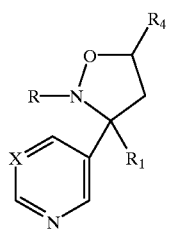

(IV)

TABLE 3

| Cmpd # | R | X | $R_1$ | $R_4$ | Physical Property |
|---|---|---|---|---|---|
| 3.1 | $CH_3$ | CH | Ph | Ph | |
| 3.2 | $CH_3$ | CH | Ph | 2-Cl(Ph) | |
| 3.3 | $CH_3$ | CH | Ph | 3-Cl(Ph) | |
| 3.4 | $CH_3$ | CH | Ph | 4-Cl(Ph) | |
| 3.5 | $CH_3$ | CH | Ph | 2-F(Ph) | |
| 3.6 | $CH_3$ | CH | Ph | 3-F(Ph) | |
| 3.7 | $CH_3$ | CH | Ph | 4-F(Ph) | |
| 3.8 | $CH_3$ | CH | Ph | 2-Br(Ph) | |
| 3.9 | $CH_3$ | CH | Ph | 3-Br(Ph) | |
| 3.10 | $CH_3$ | CH | Ph | 4-Br(Ph) | |
| 3.11 | $CH_3$ | CH | Ph | 2-$CF_3$(Ph) | |
| 3.12 | $CH_3$ | CH | Ph | 3-$CF_3$(Ph) | |
| 3.13 | $CH_3$ | CH | Ph | 4-$CF_3$(Ph) | |
| 3.14 | $CH_3$ | CH | Ph | 4-$CH_3$(Ph) | |

TABLE 3-continued

| Cmpd # | R | X | R₁ | R₄ | Physical Property |
|---|---|---|---|---|---|
| 3.15 | CH₃ | CH | Ph | 1-Naphthyl | |
| 3.16 | CH₃ | CH | Ph | 2,4-Cl(Ph) | |
| 3.17 | CH₃ | CH | Ph | 3,4-Cl(Ph) | |
| 3.18 | CH₃ | CH | Ph | 3,5-Cl(Ph) | |
| 3.19 | CH₃ | CH | Ph | 2-Pyridyl | |
| 3.20 | CH₃ | CH | Ph | 3-Pyridyl | |
| 3.21 | CH₃ | CH | Ph | 4-Pyridyl | |
| 3.22A | CH₃ | CH | Ph | CH₂—O(Ph) | 141–147, isomer A |
| 3.22B | CH₃ | CH | Ph | CH₂—O(Ph) | oil, isomer B |
| 3.23 | CH₃ | CH | Ph | CH₂—O(4-Cl(Ph)) | |
| 3.24 | CH₃ | CH | 4-Cl(Ph) | Ph | |
| 3.25 | CH₃ | CH | 4-Cl(Ph) | 2-Cl(Ph) | |
| 3.26 | CH₃ | CH | 4-Cl(Ph) | 3-Cl(Ph) | |
| 3.27 | CH₃ | CH | 4-Cl(Ph) | 4-Cl(Ph) | |
| 3.28 | CH₃ | CH | 4-Cl(Ph) | 2-F(Ph) | |
| 3.29 | CH₃ | CH | 4-Cl(Ph) | 3-F(Ph) | |
| 3.30 | CH₃ | CH | 4-Cl(Ph) | 4-F(Ph) | |
| 3.31 | CH₃ | CH | 4-Cl(Ph) | 2-Br(Ph) | |
| 3.32 | CH₃ | CH | 4-Cl(Ph) | 3-Br(Ph) | |
| 3.33 | CH₃ | CH | 4-Cl(Ph) | 4-Br(Ph) | |
| 3.34 | CH₃ | CH | 4-Cl(Ph) | 2-CF₃(Ph) | |
| 3.35 | CH₃ | CH | 4-Cl(Ph) | 3-CF₃(Ph) | |
| 3.36 | CH₃ | CH | 4-Cl(Ph) | 4-CF₃(Ph) | |
| 3.37 | CH₃ | CH | 4-Cl(Ph) | 4-CH₃(Ph) | |
| 3.38 | CH₃ | CH | 4-Cl(Ph) | 1-Naphthyl | |
| 3.39 | CH₃ | CH | 4-Cl(Ph) | 2,4-Cl(Ph) | |
| 3.40 | CH₃ | CH | 4-Cl(Ph) | 3,4-Cl(Ph) | |
| 3.41 | CH₃ | CH | 4-Cl(Ph) | 3,5-Cl(Ph) | |
| 3.42 | CH₃ | CH | 4-Cl(Ph) | 2-Pyridyl | |
| 3.43 | CH₃ | CH | 4-Cl(Ph) | 3-Pyridyl | |
| 3.44 | CH₃ | CH | 4-Cl(Ph) | 4-Pyridyl | |
| 3.45 | CH₃ | CH | 4-Cl(Ph) | CH₂—OPh | |
| 3.46 | CH₃ | CH | 4-Cl(Ph) | CH₂—O(4-Cl(Ph)) | |
| 3.47 | CH₃ | CH | 4-CF₃(Ph) | Ph | |
| 3.48 | CH₃ | CH | 4-CF₃(Ph) | 2-Cl(Ph) | |
| 3.49 | CH₃ | CH | 4-CF₃(Ph) | 3-Cl(Ph) | |
| 3.50 | CH₃ | CH | 4-CF₃(Ph) | 4-Cl(Ph) | |
| 3.51 | CH₃ | CH | 4-CF₃(Ph) | 2-F(Ph) | |
| 3.52 | CH₃ | CH | 4-CF₃(Ph) | 3-F(Ph) | |
| 3.53 | CH₃ | CH | 4-CF₃(Ph) | 4-F(Ph) | |
| 3.54 | CH₃ | CH | 4-CF₃(Ph) | 2-Br(Ph) | |
| 3.55 | CH₃ | CH | 4-CF₃(Ph) | 3-Br(Ph) | |
| 3.56 | CH₃ | CH | 4-CF₃(Ph) | 4-Br(Ph) | |
| 3.57 | CH₃ | CH | 4-CF₃(Ph) | 2-CF₃(Ph) | |
| 3.58 | CH₃ | CH | 4-CF₃(Ph) | 3-CF₃(Ph) | |
| 3.59 | CH₃ | CH | 4-CF₃(Ph) | 4-CF₃(Ph) | |
| 3.60 | CH₃ | CH | 4-CF₃(Ph) | 4-CH₃(Ph) | |
| 3.61 | CH₃ | CH | 4-CF₃(Ph) | 1-Naphthyl | |
| 3.62 | CH₃ | CH | 4-CF₃(Ph) | 2,4-Cl(Ph) | |
| 3.63 | CH₃ | CH | 4-CF₃(Ph) | 3,4-Cl(Ph) | |
| 3.64 | CH₃ | CH | 4-CF₃(Ph) | 3,5-Cl(Ph) | |
| 3.65 | C₂H₅ | CH | Ph | Ph | |
| 3.66 | C₂H₅ | CH | Ph | 2-Cl(Ph) | |
| 3.67 | C₂H₅ | CH | Ph | 3-Cl(Ph) | |
| 3.68 | C₂H₅ | CH | Ph | 4-Cl(Ph) | |
| 3.69 | C₂H₅ | CH | Ph | 2-F(Ph) | |
| 3.70 | C₂H₅ | CH | Ph | 3-F(Ph) | |
| 3.71 | C₂H₅ | CH | Ph | 4-F(Ph) | |
| 3.72 | C₂H₅ | CH | 4-Cl(Ph) | Ph | |
| 3.73 | C₂H₅ | CH | 4-Cl(Ph) | 2-CF₃(Ph) | |
| 3.74 | C₂H₅ | CH | 4-Cl(Ph) | 3-CF₃(Ph) | |
| 3.75 | C₂H₅ | CH | 4-Cl(Ph) | 4-CF₃(Ph) | |
| 3.76 | C₂H₅ | CH | 4-Cl(Ph) | 4-CH₃(Ph) | |
| 3.77 | C₂H₅ | CH | 4-Cl(Ph) | 1-Naphthyl | |
| 3.78 | C₂H₅ | CH | 4-Cl(Ph) | 2,4-Cl(Ph) | |
| 3.79 | C₂H₅ | CH | 4-Cl(Ph) | 3,4-Cl(Ph) | |
| 3.80 | C₂H₅ | CH | 4-Cl(Ph) | 3,5-Cl(Ph) | |
| 3.81 | C₂H₅ | CH | 4-Cl(Ph) | 2-Pyridyl | |
| 3.82 | C₂H₅ | CH | 4-Cl(Ph) | 3-Pyridyl | |
| 3.83 | C₂H₅ | CH | 4-Cl(Ph) | 4-Pyridyl | |
| 3.84 | C₂H₅ | CH | 4-Cl(Ph) | CH₂—OPh | |
| 3.85 | C₂H₅ | CH | 4-Cl(Ph) | CH₂—O(4-Cl(Ph)) | |
| 3.86 | CH₃ | CH | 2-Pyridyl | Ph | |
| 3.87 | CH₃ | CH | 3-Pyridyl | Ph | |
| 3.88 | CH₃ | CH | 4-Pyridyl | Ph | |
| 3.89 | CH₃ | CH | 2-Pyridyl | 2-Cl(Ph) | |
| 3.90 | CH₃ | CH | 3-Pyridyl | 3-Cl(Ph) | |
| 3.91 | CH₃ | CH | 4-Pyridyl | 4-Cl(Ph) | |
| 3.92 | C₂H₅ | CH | 3-Pyridyl | CH₂—OPh | |
| 3.93 | C₂H₅ | CH | 2-Pyridyl | CH₂—O(4-Cl(Ph)) | |
| 3.94 | CH₃ | CH | Ph | CN | |
| 3.95 | CH₃ | CH | Ph | CO₂CH₃ | |
| 3.96 | C₂H₅ | CH | Ph | CN | |
| 3.97 | C₂H₅ | CH | Ph | CO₂CH₃ | |
| 3.98 | CH₃ | CH | 4-Cl(Ph) | CN | |
| 3.99 | CH₃ | CH | 4-Cl(Ph) | CO₂CH₃ | |
| 3.100 | C₂H₅ | CH | 4-Cl(Ph) | CN | |
| 3.101 | C₂H₅ | CH | 4-Cl(Ph) | CO₂CH₃ | |
| 3.102 | CH₃ | N | Ph | Ph | |
| 3.103 | CH₃ | N | Ph | 2-Cl(Ph) | |
| 3.104 | CH₃ | N | Ph | 3-Cl(Ph) | |
| 3.105 | CH₃ | N | Ph | 4-Cl(Ph) | |
| 3.106 | CH₃ | N | Ph | 2-F(Ph) | |
| 3.107 | CH₃ | N | Ph | 3-F(Ph) | |
| 3.108 | CH₃ | N | Ph | 4-F(Ph) | |
| 3.109 | CH₃ | N | Ph | 2-Br(Ph) | |
| 3.110 | CH₃ | N | Ph | 3-Br(Ph) | |
| 3.111 | CH₃ | N | Ph | 4-Br(Ph) | |
| 3.112 | CH₃ | N | Ph | 2-CF₃(Ph) | |
| 3.113 | CH₃ | N | Ph | 3-CF₃(Ph) | |
| 3.114 | CH₃ | N | Ph | 4-CF₃(Ph) | |
| 3.115 | CH₃ | N | Ph | 4-CH₃(Ph) | |
| 3.116 | CH₃ | N | Ph | 1-Naphthyl | |
| 3.117 | CH₃ | N | Ph | 2,4-Cl(Ph) | |
| 3.118 | CH₃ | N | Ph | 3,4-Cl(Ph) | |
| 3.119 | CH₃ | N | Ph | 3,5-Cl(Ph) | |
| 3.120 | CH₃ | N | Ph | 2-Pyridyl | |
| 3.121 | CH₃ | N | Ph | 3-Pyridyl | |
| 3.122 | CH₃ | N | Ph | 4-Pyridyl | |
| 3.123 | CH₃ | N | Ph | CH₂—OPh | |
| 3.124 | CH₃ | N | Ph | CH₂—O(4-Cl(Ph)) | |
| 3.125 | CH₃ | N | 4-Cl(Ph) | Ph | |
| 3.126 | CH₃ | N | 4-Cl(Ph) | 2-Cl(Ph) | |
| 3.127 | CH₃ | N | 4-Cl(Ph) | 3-Cl(Ph) | |
| 3.128 | CH₃ | N | 4-Cl(Ph) | 4-Cl(Ph) | |
| 3.129 | CH₃ | N | 4-Cl(Ph) | 2-F(Ph) | |
| 3.130 | CH₃ | N | 4-Cl(Ph) | 3-F(Ph) | |
| 3.131 | CH₃ | N | 4-Cl(Ph) | 4-F(Ph) | |
| 3.132 | CH₃ | N | 4-Cl(Ph) | 2-Br(Ph) | |
| 3.133 | CH₃ | N | 4-Cl(Ph) | 3-Br(Ph) | |
| 3.134 | CH₃ | N | 4-Cl(Ph) | 4-Br(Ph) | |
| 3.135 | CH₃ | N | 4-Cl(Ph) | 2-CF₃(Ph) | |
| 3.136 | CH₃ | N | 4-Cl(Ph) | 3-CF₃(Ph) | |
| 3.137 | CH₃ | N | 4-Cl(Ph) | 4-CF₃(Ph) | |
| 3.138 | CH₃ | N | 4-Cl(Ph) | 4-CH₃(Ph) | |
| 3.139 | CH₃ | N | 4-Cl(Ph) | 1-Naphthyl | |
| 3.140 | CH₃ | N | 4-Cl(Ph) | 2,4-Cl(Ph) | |
| 3.141 | CH₃ | N | 4-Cl(Ph) | 3,4-Cl(Ph) | |
| 3.142 | CH₃ | N | 4-Cl(Ph) | 3,5-CT(Ph) | |
| 3.143 | CH₃ | N | 4-Cl(Ph) | 2-Pyridyl | |
| 3.144 | CH₃ | N | 4-Cl(Ph) | 3-Pyridyl | |
| 3.145 | CH₃ | N | 4-Cl(Ph) | 4-Pyridyl | |
| 3.146 | CH₃ | N | 4-Cl(Ph) | CH₂—OPh | |
| 3.147 | CH₃ | N | 4-Cl(Ph) | CH₂—O(4-Cl(Ph)) | |
| 3.148 | CH₃ | N | 4-CF₃(Ph) | Ph | |
| 3.149 | CH₃ | N | 4-CF₃(Ph) | 2-Cl(Ph) | |
| 3.150 | CH₃ | N | 4-CF₃(Ph) | 3-Cl(Ph) | |
| 3.151 | CH₃ | N | 4-CF₃(Ph) | 4-Cl(Ph) | |
| 3.152 | CH₃ | N | 4-CF₃(Ph) | 2-F(Ph) | |
| 3.153 | CH₃ | N | 4-CF₃(Ph) | 3-F(Ph) | |
| 3.154 | CH₃ | N | 4-CF₃(Ph) | 4-F(Ph) | |
| 3.155 | CH₃ | N | 4-CF₃(Ph) | 2-Br(Ph) | |
| 3.156 | CH₃ | N | 4-CF₃(Ph) | 3-Br(Ph) | |
| 3.157 | CH₃ | N | 4-CF₃(Ph) | 4-Br(Ph) | |
| 3.158 | CH₃ | N | 4-CF₃(Ph) | 2-CF₃(Ph) | |
| 3.159 | CH₃ | N | 4-CF₃(Ph) | 3-CF₃(Ph) | |
| 3.160 | CH₃ | N | 4-CF₃(Ph) | 4-CF₃(Ph) | |
| 3.161 | CH₃ | N | 4-CF₃(Ph) | 4-CH₃(Ph) | |
| 3.162 | CH₃ | N | 4-CF₃(Ph) | 1-Naphthyl | |
| 3.163 | CH₃ | N | 4-CF₃(Ph) | 2,4-Cl(Ph) | |
| 3.164 | CH₃ | N | 4-CF₃(Ph) | 3,4-Cl(Ph) | |
| 3.165 | CH₃ | N | 4-CF₃(Ph) | 3,5-Cl(Ph) | |
| 3.166 | C₂H₅ | N | Ph | Ph | |

TABLE 3-continued

| Cmpd # | R | X | $R_1$ | $R_4$ | Physical Property |
|---|---|---|---|---|---|
| 3.167 | $C_2H_5$ | N | Ph | 2-Cl(Ph) | |
| 3.168 | $C_2H_5$ | N | Ph | 3-Cl(Ph) | |
| 3.169 | $C_2H_5$ | N | Ph | 4-Cl(Ph) | |
| 3.170 | $C_2H_5$ | N | Ph | 2-F(Ph) | |
| 3.171 | $C_2H_5$ | N | Ph | 3-F(Ph) | |
| 3.172 | $C_2H_5$ | N | Ph | 4-F(Ph) | |
| 3.173 | $C_2H_5$ | N | 4-Cl(Ph) | Ph | |
| 3.174 | $C_2H_5$ | N | 4-Cl(Ph) | 2-$CF_3$(Ph) | |
| 3.175 | $C_2H_5$ | N | 4-Cl(Ph) | 3-$CF_3$(Ph) | |
| 3.176 | $C_2H_5$ | N | 4-Cl(Ph) | 4-$CF_3$(Ph) | |
| 3.177 | $C_2H_5$ | N | 4-Cl(Ph) | 4-$CH_3$(Ph) | |
| 3.178 | $C_2H_5$ | N | 4-Cl(Ph) | 1-Naphthyl | |
| 3.179 | $C_2H_5$ | N | 4-Cl(Ph) | 2,4-Cl(Ph) | |
| 3.180 | $C_2H_5$ | N | 4-Cl(Ph) | 3,4-Cl(Ph) | |
| 3.181 | $C_2H_5$ | N | 4-Cl(Ph) | 3,5-Cl(Ph) | |
| 3.182 | $C_2H_5$ | N | 4-Cl(Ph) | 2-Pyridyl | |
| 3.183 | $C_2H_5$ | N | 4-Cl(Ph) | 3-Pyridyl | |
| 3.184 | $C_2H_5$ | N | 4-Cl(Ph) | 4-Pyridyl | |
| 3.185 | $C_2H_5$ | N | 4-Cl(Ph) | $CH_2$—OPh | |
| 3.186 | $C_2H_5$ | N | 4-Cl(Ph) | $CH_2$—O(4-Cl(Ph)) | |
| 3.187 | $CH_3$ | N | 2-Pyridyl | Ph | |
| 3.188 | $CH_3$ | N | 3-Pyridyl | Ph | |
| 3.189 | $CH_3$ | N | 4-Pyridyl | Ph | |
| 3.190 | $CH_3$ | N | 2-Pyridyl | 2Cl-Ph | |
| 3.191 | $CH_3$ | N | 3-Pyridyl | 3Cl-Ph | |
| 3.192 | $CH_3$ | N | 4-Pyridyl | 4Cl-Ph | |
| 3.193 | $C_2H_5$ | N | 3-Pyridyl | $CH_2$—OPh | |
| 3.194 | $C_2H_5$ | N | 4-Pyridyl | $CH_2$—O(4-Cl(Ph)) | |
| 3.195 | $CH_3$ | N | Ph | CN | |
| 3.196 | $CH_3$ | N | Ph | $CO_2$CH8 | |
| 3.197 | $C_2H_5$ | N | Ph | CN | |
| 3.198 | $C_2H_5$ | N | Ph | $CO_2CH_3$ | |
| 3.199 | $CH_3$ | N | 4-Cl(Ph) | CN | |
| 3.200 | $CH_3$ | N | 4-Cl(Ph) | $CO_2CH_3$ | |
| 3.201 | $C_2H_5$ | N | 4-Cl(Ph) | CN | |
| 3.202 | $C_2H_5$ | N | 4-Cl(Ph) | $CO_2CH_3$ | |

As used in Tables 1 to 3 Ph is understood to be phenyl.

Scheme A describes the general procedure for the preparation of compounds of the Formula (I). These 3-heterocyclic-3,4,5-substituted isoxazolidines are prepared by the reaction of nitrones (V) with substituted alkenes (VI). The 1,3-dipolar cycloaddition of nitrones to alkenes is described in *Advances in Heterocyclic Chemistry*, Vol 21., pp.207–251, 1977; *Angewandte Chem. Int. Ed*, Vol. 2, 565–598, 1963; Synthesis, 205–221, 1975 and in *J. Org. Chemistry*, Vol. 49, 276–1281, 1984 and references cited therein. The cycloaddition can proceed to provide two regioisomers one of which is shown in Scheme A of formula I where $R_4$ and $R_5$ are bonded to the carbon adjacent to the oxygen of the isoxazolidine. The other regioisomer, where $R_2$ and $R_3$ are bonded to the carbon adjacent to the oxygen of the isoxazolidine are also the subject of this invention. The regioisomers, when formed can be separated by conventional techniques such as thin layer or column chromatography. The reaction of N-substituted-3,3-disubstituted nitrones of formula V or V' are conducted in solvents such as benzene, toluene and chlorobenzene at temperatures of 50° C. to the solvent boiling point and preferably at reflux in toluene. The olefins utilized can be tetrasubstituted olefins (VI), as shown in scheme A but are most often α,α-disubstituted olefins (VI where $R_2$, $R_3$=H) and monosubstituted olefins (VI' where $R_4$=H) such as substituted styrenes, allylethers and acrylates. The isoxazolidines of the present invention can exist in diastereomeric forms. For example when monosubstituted olefins are employed the substituents H and $R_5$ can be cis or trans to the C-3 heterocycle. The cis and trans isomers can be separated by standard chromatographic techniques. When separated the isomers are designated isomer A or isomer B with isomer A possessing the higher Rf on thin layer chromatography.

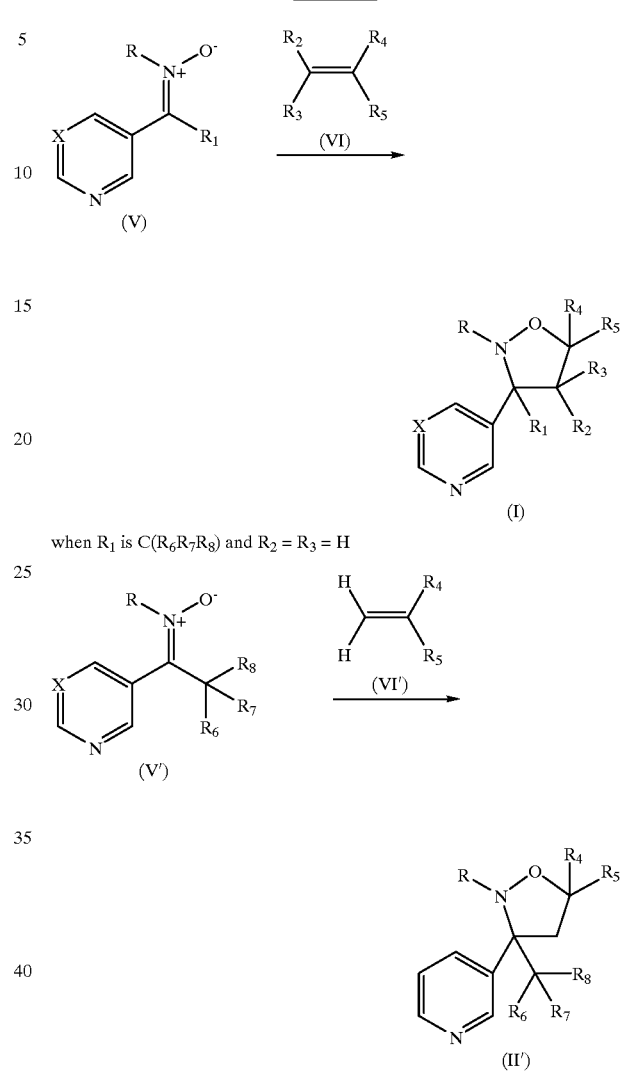

Scheme B describes the general procedure for the preparation of nitrones V and V'. The nitrones of the present invention are N-substituted-α,α-disubstituted such that the alpha substituents must be non-hydrogen substituents. The chemistry of nitrones, both preparations and reactions, are described in *Chem Reviews*, Vol. 64, 473–495, 1964. The nitrones of the present invention are derived from ketones which bear one heterocycle in the form of 3-pyridyl or 5-pyrimidinyl rings and the other substituent as $R_1$ defined previously. The nitrones are prepared from the corresponding ketone in a hydroxylic solvent such as methanol or ethanol, preferably ethanol, at room temperature to reflux, preferably at room temperature, by the reaction with an R—NHOH for example N-methylhydroxylamine in the form of the hydrochloride salt in the presence of sodium acetate. The nitrone is isolated by removing the solvent followed by trituration of the resulting wet solid with methylene chloride with isolation of the nitrone from the filtrate. The nitrones are used directly in the cycloaddition reactions described in scheme A.

Scheme B

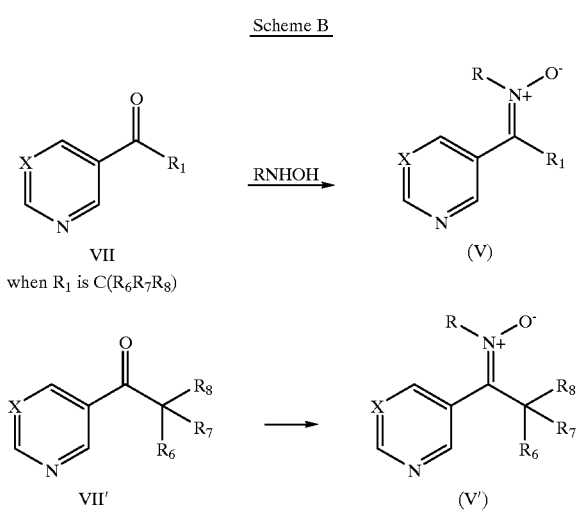

VII when R₁ is C(R₆R₇R₈)

The ketones of formula VII and VII' bearing a 3-pyridyl or 5-pyrimidinyl substituents can be prepared by standard synthesis techniques or in the case of 3-acetylpyridine is commercially available. For example March, *Advanced Organic Chemistry*, 4th Ed, pp. 963–965, and references cited therein, describe the preparation of ketones from nitrites by addition of a Grignard reagent, RMgBr, or an organolithium such as RLi.

Pyridyl ketones can be prepared by Friedel Crafts acylation as described in *Organic Synthesis*, Vol. 37, 1957, by magnesium catalyzed acylation to form acetylpyridines as described in *Tetrahedron* Vol. 48, pp.9233–9236, 1992, and from pyridyl esters by classical Claisen condensation as described in *JACS*, Vol. 69, 119, 1947 and Vol. 76, 5452, 1954. When the reaction of the nitrones, V and V', with olefins (VI and VI') provides incomplete conversion to the isoxazolidines (I), mixtures of (I) and (VII) are isolated. To remove the unwanted ketones VII and VII' the mixture is exposed to an alkylhydroxylamine in an alcoholic solvent in the presence of sodium acetate and is stirred at room temperature. The solvent is removed and the residue is dissolved in an organic solvent which is washed thoroughly with water. The water soluble nitrone is removed in the aqueous phase and the resulting organic phase contains the pure desired product.

The compounds of this invention can be made according to the following procedures:

EXAMPLE 1

5-(4-chlorophenyl)-2,3-dimethyl-3-(3-pyridyl) isoxazolidine (Compounds 1.4, 1.4A and 1.4B of Table I)

In a 500 ml 3-necked RB flask was added 35 g (0.233 mol) of 3-pyridyl-N-methyl ethylimine N-oxide and 32.3 g of p-chlorostyrene (0.233 mol, 1 eq.) in 200 mL toluene and was heated to reflux (110° C.) for 5 hours. The reaction is monitored by Thin Layer Chromatography (TLC) (1:1 Hex/EtOAc). Upon consumption of the p-chlorostyrene the reaction was cooled to room temperature. The toluene was extracted with 300 mL of 10% HCl, then 100 mL of 10% HCl. The acid layer was then washed once with 100 mL toluene. The toluene portion was discarded and the acid portion was taken to pH 6 with 10% NaOH. This aqueous portion was extracted with several 200 ml portions of ethyl acetate. Washed the EtOAc with water and brine, dried over anhydrous sodium sulfate, filtered and stripped to yield an 32 g of an orange oil which was a mixture of the desired product and 3-acetylpyridine.

The crude reaction mixture was purified by the following process. 32 g of the crude mixture as an orange oil was treated with 10 g of N-methylhydroxylamine hydrochloride, and 20 g of sodium acetate in a 500 mL RB flask with 100 mL of absolute ethanol. The reaction mixture was stirred overnight at room temperature. The solvent was removed and the residue was dissolved in 150 mL of ethyl acetate which was wased with 2×100 mL water and 1×100 mL brine. The solvent was dried over anhydrous sodium sulfate, filtered and stripped to yield 15.6 g of an orange oil whose 300 MHz $^1$H NMR was consistent with 5-(4-chlorophenyl)-2,3-dimethyl-3-(3-pyridyl)isoxazolidine as a 2:1 mixture of isomer A (higher Rf on TLC): isomer B (lower Rf on TLC).

NMR ($^1$H, 200 MHz) of Compound 1.04: 1.6–1.7(two singlets, 3H), 2.6(two singlets, 3H), 2.3–2.9(m, 2H), 4.9–5.4 (two dd, 1H), 7.0–7.4(m 5H), 7.8–8.0(two dd,1H), 8.5–8.6 (two dd, 1H) and 8.75 and 8.85 (two dd,1H).

8 g of the crude mixture was purified by silica gel column chromatography with 1:1 hexane:EtOAc and gave 1.2 g of 9:1 A:B isomers as a clear oil, 0.4 g of 4:1 A:B isomers as a clear oil, 0.2 g of 1:6 A:B isomer as a white solid, mp. 75° C.–80° C. and 2.0 g of 4:5 mixture of A:B isomers as a mixture od solid and oil (52.5% yield based on 8 g purified).

NMR ($^1$H, 200 MHz) 9:1 isomers A:B, major isomer A, Compound 1.04A: 1.6(s, 3H), 2.6(s, 3H), 2.5–2.9(m, 2H), 5.2–5.4(dd, 1H), 7.0–7.4(m 5H), 7.8–7.9(d,1H), 8.5(d, 1H) and 8.75(d,1H).

NMR ($^1$H, 200 MHz) 1:5 isomers A:B, major isomer B, Compound 1.04B: 1.55(s, 3H), 2.6(s, 3H), 2.3–2.9(m, 2H), 4.85–5.0(t, 1H), 7.0–7.4(m 5H), 7.9–8.0(d,1H), 8.6(d, 1H) and 8.85(d,1H).

Synthesis of Nitrone, 3-pyridyl-N-methyl ethylimine N-oxide

3-Acetylpyridine (80 g, 0.661 mol), N-methylhydroxylamine hydrochloride (84 g, 1.018 mol, 1.5 eq) and sodium acetate (164.8 g, 2.01 mol, 3 eq) were combined in a 1 L rbf with 450 mL of absolute ethanol. Let stir overnight. Reaction monitored by TLC (1:1 EtAc/Hexanes). Watch for the disappearance of the 3-Acetylpyridene spot and the formation of a spot on the baseline (presumably the nitrone). Stripped off the ethanol. Took up the residue in 400 mL of methylene chloride. Filtered off remaining residue. Dried over anhydrous sodium sulfate, filtered and stripped to yield a light yellow oil. Yield for this run was 94 g (95%).

EXAMPLE 2

5-phenoxymethyl-3-phenyl-3-(3-pyridyl)-2-methyl isoxazolidine Compounds 3.22A, 3.22B of Table 3

Into a 300 ml 3-neck RB flask under nitrogen was added 2.1 g (1.0 eq., 10 mmole) 3-pyridyl-N-methyl benzylimine N-oxide in 25 ml toluene and 4.0 g (3.0 eq., 30 mmole) of allyl phenyl ether in 25 ml toluene and heated at reflux (110° C.). After one day, the following additional starting reagents were added to the flask: 1.05 g (1.0 eq., 5 mmole) of the N-oxide and 2.0 g (3.0 eq., 15 mmole) of the ether. Heated at reflux for 6 days and worked up. In the work up the reaction solution was concentrated on the rotovap at 50° C. to give 6.6 g wet solid containing a mixture of stereoisomers. Triturated the wet solid with ethyl acetate/hexane and vacuum filtered to give 1.8 g isomer A (upper spot, Rf=0.59 ethyl acetate/hexane 1:1) product as a solid, mp=145° C.–147° C.

NMR (¹H, 200 MHz) of Compound 3.22A: 2.5(s, 3H); 3.0(s, 1H); 3.3(s, 1H); 3.7–4.1(m, 2H); 4.65 (s, 1H); 6.8–7.4(m 11H); 7.85(d,1H), 8.5(dd, 1H); 8.65(d,1H).

Concentrated the filtrate to give 4.5 g yellow oil and chromatographed (ethyl acetate/hexane 1:1) to give 0.7 g isomer B (Rf=0.47 ethyl acetate/hexane 1:1) product as a yellow oil.

NMR (¹H, 200 MHz) of Compound 3.22B: 2.5(s, 3H); 3.1(s, 2H); 4.1(s, 2H); 4.4(s,1H); 6.85–7.4(m,11H); 7.9(s, 1H); 8.5(dd, 1H); 8.65(d,1H).

Preparation of 3-pyridyl-N-methyl benzylimine N-oxide

Into a 300 ml 3-neck RB flask under $N_2$ was added 9.15 g (1.0 eq., 0.050 moles) 3-benzoylpyridine in 50 ml absolute ethanol and dissolved. Added neat 5.0 g (1.2 eq., 0.060 moles) N-methyl hydroxylamine hydrochloride followed by 9.84 g (2.4 eq., 0.12 moles) acetic acid, sodium salt. The reaction was stirred 88 h at ambient and refluxed (78° C.) for 20 h followed by workup. The reaction solution was made basic to pH 8 with potassium carbonate, filtered off solid, and concentrated the filtrate to give an orange wet solid. Triturated the wet solid with methylene chloride, filtered, dried filtrate over magnesium sulfate, anhyd., and concentrated to give 11.3 g orange solid, 60% product and 40% starting ketone by GC. Triturated the crude solid with ethyl acetate and filtered to give 2.4 g product as a white solid, mp=143° C.–146° C. A second crop of 1.5 g of slightly less purity was isolated from the filtrate after concentrating and trituration. Total product was 3.9 g (36.8% yield).

NMR(¹H, 200 MHz): 3.8(s,3H); 7.2–7.6(m,6H); 8.6(d, 1H); 8.8(dd, 1H); 8.9 (d,1H).

EXAMPLE 3

Proton NMR data (200 MHz) are Provided in Table IV for Typical Representative Compounds of Tables I and II

TABLE IV

| Compd # | Proton NMR δ (chemical shifts rel. to TMS) |
| --- | --- |
| 1.4A | 1.6(s, 3H), 2.6(s, 3H), 2.5–2.9(m, 2H), 5.2–5.4(dd, 1H), 7.0–7.4(m, 5H), 7.8–7.9(d,1H), 8.5(d, 1H) and 8.75(d, 1H). |
| 1.4 | 1.6–1.7(two singlets, 3H), 2.6( two singlets, 3H), 2.3–2.9(m, 2H), 4.9–5.4 (two dd, 1H), 7.0–7.4(m 5H), 7.8–8.0(two dd, 1H), 8.5–8.6(two dd, 1H)and 8.75 and 8.85 (two dd, 1H). |
| 1.4B | 1.55(s, 3H), 2.6(s, 3H), 2.3–2.9(m, 2H), 4.85–5.0(t, 1H), 7.0–7.4(m, 5H), 7.9–8.0(d, 1H), 8.6(d, 1H) and 8.85(d, 1H). |
| 3.22A | 2.5(s, 3H); 3.0(s, 1H); 3.3(s, 1H); 3.7–4.1(m, 2H); 4.65 (s, 1H); 6.8–7.4 (m 11H); 7.85(d, 1H), 8.5(dd, 1H); 8.65(d, 1H). |
| 3.22B | 2.5(s, 3H); 3.1(s, 2H); 4.1(s, 2H); 4.4(s, 1H); 6.85–7.4(m, 11H); 7.9(s, 1H); 8.5(dd, 1H); 8.65(d, 1H). |
| 1.6 | 1.6(s, 3H), 2.6(d, 3H), 2.6–2.9(m, 2H), 5.2–5.3(dd, 1H), 6.9–7.4(m 5H), 7.9 (dd, 1H), 8.5(d, 1H) and 8.8(d, 1H). |
| 1.23A | 1.6(s, 3H), 2.2(d, 6H), 2.6(d, 3H), 2.3–2.9(m, 2H), 5.5(dd, 1H), 6.9–7.5 (m 4H), 7.8 (dd, 1H), 8.5(d, 1H) and 8.85(s, 1H). |
| 1.23 | 1.6(two singlets, 3H), 2.2(d, 6H), 2.6(d, 3H), 2.3–2.9(m, 2H), 5.2–5.4(two multiplets, 1H), 6.9–7.5(m, 4H), 7.8–7.9 (two multiplets, 1H), 8.4–8.5(two doublets, 1H) and 8.7–8.9(two singlets, 1H). |
| 1.2 | 1.5–1.6(two singlets, 3H), 2.6(br s, 3H), 2.3–2.9(m, 2H), 5.25–5.3 and 5.4–5.5(br m and dd, 1H), 7.0–7.4(m, 4H), 7.7–7.8 (two d, 1H), 8.4–8.5(two doublets, 1H) and 8.7–8.9(two singlets, 1H). |
| 1.3 | 1.5–1.6(two singlets, 3H), 2.6(br s, 3H), 2.3–2.9(m, 2H), 5.0–5.1 and 5.2–5.3(br m and dd, 1H), 7.0–7.4(m, 5H), 7.8–7.9 (two d, 1H), 8.4–8.5 (two doublets, 1H) and 8.7–8.85(two singlets, 1H). |

TABLE IV-continued

| Compd # | Proton NMR δ (chemical shifts rel. to TMS) |
| --- | --- |
| 1.7 | 1.59–1.60(two singlets, 3H), 2.63(br s, 3H), 2.3–2.9(m, 2H), 5.0–5.1 and 5.2–5.3(br m and dd, 1H), 6.9–7.4(m, 5H), 7.8–8.0 (two d, 1H), 8.5–8.6(two doublets, 1H) and 8.74–8.85(two singlets, 1H). |
| 1.1 | 1.60–1.62(two singlets, 3H), 2.62, 2.65(two singlets, 3H), 2.3–2.9(m, 2H), 5.0–5.1 and 5.2–5.3(br m and dd, 1H), 7.1–7.4(m, 6H), 7.85–8.0(two d, 1H), 8.5–8.6(two doublets, 1H) and 8.74–8.85(two singlets, 1H). |
| 1.5 | 1.56–1.62(two singlets, 3H), 2.62, 2.65(two singlets, 3H), 2.3–2.9(two dd, 2H), 5.0–5.1 and 5.2–5.3(br m and dd, 1H), 6.9–7.65(m, 5H), 7.85–7.95 (two d, 1H), 8.45–8.55(two doublets, 1H) and 8.7–8.85(two singlets, 1H). |
| 1.15 | 1.60–1.62(two singlets, 3H), 2.09, 2.17(two singlets, 3H), 2.64–2.67(br d, 3H), 2.3–2.9(two dd, 2H), 5.0–5.1 and 5.2–5.3(br m and dd, 1H), 6.9–7.35(m, 5H), 7.85–7.95 (two d, 1H), 8.5–8.55(two doublets, 1H) and 8.7–8.85(two singlets, 1H). |
| 1.10 | 1.57–1.60(two singlets, 3H), 2.61–2.63(two singlets, 3H), 2.3–2.9(two dd, 2H), 4.9–5.1 and 5.2–5.3(br m and dd, 1H), 7.1–7.65(m, 5H), 7.85–7.95 (two d, 1H), 8.5–8.55(two doublets, 1H) and 8.72–8.8(two singlets, 1H). |
| 1.13 | 1.57–1.62(two singlets, 3H), 2.61–2.63(two singlets, 3H), 2.3–2.9(two dd, 2H), 5.0–5.1 and 5.2–5.3(br m and dd, 1H), 7.3–7.65(m, 5H), 7.85–7.95 (two d, 1H), 8.5–8.55(two doublets, 1H) and 8.7–8.8(two singlets, 1H). |
| 1.9 | 1.58–1.62(two singlets, 3H), 2.6–2.63(two singlets, 3H), 2.3–2.9(two dd, 2H), 5.0–5.1 and 5.2–5.3(br m and dd, 1H), 7.1–7.5(m, 5H), 7.85–7.95 (two d, 1H), 8.5–8.55(two doublets, 1H) and 8.7–8.8(two singlets, 1H). |
| 1.39 | 1.23–1.30(m, 6H, NCH$_2$CH$_3$, C-3 CH$_3$), 2.2–2.6(m, 2H), 2.7–3.0(m, 2H, NCH$_2$CH$_3$), 5.0–5.1 and 5.2–5.3(br m and dd, 1H), 7.1–7.5(m, 5H), 7.85–7.95 (two d, 1H), 8.5–8.6(two doublets, 1H) and 8.7–8.8(two singlets, 1H). |
| 1.51 | 1.23–1.30(m, 9H), 2.2–2.6(m, 2H), 2.9–3.0(m, 1H), 5.0–5.1 and 5.2–5.3(br m and dd, 1H), 7.1–7.5(m, 4H), 7.8–8.0 (four d, 1H), 8.5–8.6(two doublets, 1H) and 8.7–8.8(two singlets, 1H). |
| 1.63 | 1.1–1.9(m, 13H), 2.1–2.6(two dd, 2H), 2.7–2.9(m, 1H), 4.9–5.0 and 5.1–5.2(br m and m, 1H), 7.2–7.5(m, 5H), 7.85–7.95 (two d, 1H), 8.6(d, 1H) and 8.9(s, 1H). |

Note:
¹HNMR spectrum was recorded, using CDCl$_3$.
Following codes were used s = singlet, d = doublets, t = triplets, m = multiplets, br = broad peak

EXAMPLE 4

Numerous compounds of this invention were tested for fungicidal activity in vivo against the diseases described below. The compounds were dissolved in a 1:1 mixture of acetone and methanol or N,N-dimethylformamide and diluted with a 2:1:1 mixture of water, acetone and methanol (by volume) to achieve the appropriate concentration. The solution was sprayed onto plants and allowed to dry for two hours. Then the plants were inoculated with fungal spores. Each test utilized control plants which were sprayed with the appropriate solvent and inoculated. For these protective tests, the plants were inoculated one day after treating the plants with the compounds of this invention. The remainder of the technique of each of the tests is given below along with the results for various compounds described herein by the Compound # against the various fungi at a dose of 100 or 150 grams per hectare. The results are percent disease control as compared to the untreated check wherein one hundred was rated as complete disease control and zero as no disease control. The percent disease control is reported in activity groups wherein A is 90–100% disease control, B is 70–89% control, C is 50–69% control and D is less than 50% disease control The application of the test fungal spores to the test plants was as follows:

Wheat Leaf Blotch (SNW)

Cultures of *Septoria nodorum* were maintained on Czapek-Dox V-8 juice agar plates in an incubator at 20° C. with alternating periods of 12 hours of light and 12 hours of darkness for 2 weeks. A water suspension of the spores was obtained by shaking the portion of the plate with fungal material in deionized water and filtering through cheesecloth. The spore-containing water suspension was diluted to a spore concentration of $3.0 \times 10^6$ spores per ml. The inoculum was dispersed by a DeVilbiss atomizer over one-week old Fielder wheat plants which had been previously sprayed with the fungicide compound. The inoculated plants were placed in a humidity cabinet at 20° C. with alternating 12 hours of light and 12 hours of darkness for 7 days. The inoculated seedlings were then moved to a controlled environment room at 20° C. for 2 days of incubation. Disease control values were recorded as percent control.

Wheat Powdery Mildew (WPM)

*Erysiphe graminis* (f. sp. tritici) was cultured on wheat seedlings, cultivar Fielder, in a controlled temperature room at 18° C. Mildew spores were shaken from the culture plants onto 7-day old wheat seedlings which had been previously sprayed with the fungicide compound. The inoculated seedlings were kept in a controlled temperature room at 18° C. and subirrigated. The percent disease control was rated 7 days after the inoculation.

Cucumber Powdery Mildew (CPM)

*Sphaerotheca fulginea* was maintained on cucumber plants, cultivar Bush Champion, in the greenhouse. Inoculum was prepared by placing five to ten heavily mildewed leaves in a glass jar with 500 ml of water containing 1 drop of Tween 80 per 100 ml. After shaking the liquid and leaves, the inoculum was filtered through cheese cloth and misted onto the plants with a squirt bottle mister. The spore count was 100,000 spores/ml. The plants were then placed in the greenhouse for infection and incubation. The plants were scored seven days after inoculation. Disease control values were recorded as percent control.

Rice Blast (RB)

Cultures of *Pyricularia oyrzae* were maintained on potato dextrose agar for two to three weeks. The spores were washed from the agar with water containing 1 drop of Tween 80 per 100 ml. After filtering the spore suspension through two layers of cheese cloth, the spore count was adjusted to $5 \times 10^5$ spores/ml. The spore suspension was sprayed onto 12-day old rice plants, cultivar M-1, using a DeVilbiss atomizer. The inoculated plants were placed in a humidity at chamber 20° C. for 36 hours to allow for infection. After the infection period the plants were placed in the greenhouse. After 6 days, the plants were scored for disease control.

Botrytis on Cucumber (BOT)

Cucumber plants were maintained in the greenhouse. Large, fully expanded leaves were collected from the plates. The stems were wrapped with cotton, the leaves were placed in a large petri plate (15-cm. diameter) and the leaves were supported by glass rods. The upper cover of the plate was removed and the upper surface of the detached cucumber leaf was sprayed with the compounds of the present invention. The leaf was allowed to dry in the air for approximately 2 hours. The cultures of *Botrytis cinerea* were maintained on potato dextrose agar for two to three weeks. Agar plugs, 6-mm. in diameter, were cut with a cork borer from the periphery of the fungal colony margin. These agar plugs were placed with the fungal surface in contact with the treated upper surface of the cucumber leaf. Each leaf received two mycelial plugs. After placing the petri plate cover over the leaves, the plates were returned to a controlled environmental chamber at 20° C. and 90% humidity for three to four days. After this time, the diameter of the lesions produced by the mycelial plug was measured. The average lesion size was compared to the lesion size produced on the control leaves. Data were expressed as percent control.

Cucumber Downy Mildew (CDM)

Cucumber plants were maintained in the greenhouse. Large, fully expanded leaves were collected from the plates. The stems were wrapped with cotton, the leaves were placed in a large petri plate (15-cm. diameter) and the leaves were supported by glass rods. The upper cover of the plate was removed and the upper surface of the detached cucumber leaf was sprayed with the compounds of the present invention. The leaf was allowed to dry in the air for approximately 2 hours. The cultures of *Pseudoperonospora cubensis* were maintained on cucumber plants. After extracting the spores by shaking the leaves in water, the lower surface of the treated cucumber leaves were sprayed with a spore concentration of 100,000 spores per ml. The plates were returned to a controlled environmental chamber at 20° C. and 90% humidity for five days. After this time, leaves were examined for disease development. Data was expressed as percent control.

When tested against wheat leaf blotch at 300 grams per hectare compound 1.7 exhibited control in the B rating group When tested against wheat powdery mildew at 300 grams per hectare compounds 1.04A, 1.10, and 1.51 exhibited control in the A rating group and compounds 1.7, 1.13 and 1.63 exhibited control in the B rating group.

When tested against cucumber powdery mildew at a dose of 300 grams per hectare, 1.04 exhibited control in the A rating group and 1.23 in the B rating group.

When tested against rice blast at 300 grams per hectare compounds 1.04, 1.10, 1.39 and 1.51 exhibited control in the B rating group.

When tested against cucumber gray mold at 300 grams per hectare compounds 1.04A, 1.9 and 1.10 exhibited control in the A rating group and 1.13, 1.39 and 1.51 exhibited control in the B rating group.

When tested against cucumber downy mildew at 300 grams per hectare compounds 1.04A, 1.15 and 1.51 exhibited control in the A rating group.

The compounds of this invention are useful as agricultural fungicides and, as such, can be applied to various loci such as the seed, the soil or the foliage of plants to be protected.

The compounds of this invention can be applied as fungicidal sprays by methods commonly employed, such as conventional high-volume hydraulic sprays, low-volume sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15). Other known fungicides which an be combined with the compounds of this invention are dimethomorph, cymoxanil, thifluzamide, furalaxyl, ofurace, benalaxyl, oxadixyl, propamocarb, cyprofuram, fenpiclonil, fludioxonil, pyrimethanil, cyprodinil, triticonazole, fluquinconazole, metconazole, spiroxamine, carpropamid, azoxystrobin, kresoxim-methyl, metominostrobin and trifloxystrobin.

The compounds of this invention can be advantageously employed in various ways. Since these compounds possess broad spectrum fungicidal activity, they can be employed in the storage of cereal grain. These compounds can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, barley stripe and leaf rust, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse or diffuse the active ingredient in the composition without impairing the active ingredient's effectiveness and which by itself has no significant detrimental effect on the soil, equipment, desirable plants, or agronomic environment. If desired, adjuvants such as surfactants, stabilizers, antifoam agents and anti-drift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. A listing of such adjuvants commonly used in the art, and a discussion of adjuvants, can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents; especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001 (1:999,999)–99 (99:1) % by weight. For compositions suitable for storage or transportation, the amount of active ingredient is preferably between about 0.5 (1:199)–90 (9:1) % by weight, and more preferably between about 1 (1:99) –75 (3:1) % by weight of the mixture. Compositions suitable for direct application or field application generally contain the active compound in an amount substantially between about 0.0001 (1:999,999)–95 (19:1) %, preferably between about 0.0005 (1:199,999)–90 (9:1) % by weight, and more preferably between about 0.001 (1:99,999)–75 (3:1) % by weight of the mixture. The composition can also be stated as a ratio of the compound to the carrier. In the present invention the weight ratio of these materials (active compound/carrier) can vary from 99:1 (99%) to 1:4 (20%) and more preferably from 10:1 (91%) to 1:3 (25%).

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clay, inorganic silicate and carbonate, and silica and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a compound of Formula I, 45 parts of a synthetic precipitated hydrated silicon dioxide, such as that sold under the trademark Hi-SilR, available from PPG Industries, Pittsburgh, Pa., and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®3.

Dusts are prepared by mixing compounds of Formula I, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which comprises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:

1. A compound of the formula:

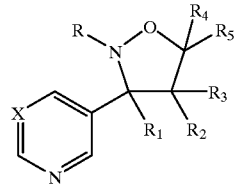

I

X is CH or nitrogen;

R is selected from the group consisting of $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$alkynyl, $(C_1-C_{12})$alkoxy$(C_1-C_{12})$alkyl, $(C_3-C_7)$cycloalkyl, halo$(C_3-C_7)$cycloalkyl, $(C_3-C_7)$cycloalkyl$(C_1-C_4)$alkyl, aralkyl, aryloxy$(C_1-C_4)$alkyl and heterocyclic;

$R_1$ is selected from the group consisting of aryl, heterocyclic, and $C(R_6R_7R_8)$ $R_2$ and $R_3$ are each independently selected from the group consisting of hydrogen, $(C_1-C_{12})$alkyl, halo$(C_1-C_{12})$alkyl, $(C_1-C_{12})$alkoxy, halo$(C_1-C_{12})$alkoxy, $(C_3-C_7)$cycloalkyl, $(C_3-C_7)$cycloalkyl$(C_1-C_4)$alkyl, aryl, aralkyl, heterocyclic; cyano, and $(C_1-C_4)$alkoxycarbonyl;

$R_4$ and $R_5$ are selected from the group consisting of hydrogen, $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo $(C_2-C_8)$alkynyl, $(C_3-C_7)$cycloalkyl, halo$(C_3-C_7)$ cycloalkyl, $(C_3-C_7)$cycloalkyl$(C_1-C_4)$alkyl, aryl, aryloxy$(C_1-C_4)$alkyl, aralkyl, heterocyclic, cyano, and $(C_1-C_4)$alkoxycarbonyl such that $R_4$ and $R_5$ are not both hydrogen;

$R_6$, $R_7$, and $R_8$ are each independently selected from the group consisting of hydrogen, $(C_1-C_{12})$alkyl, $(C_2-C_8)$ alkenyl, $(C_2-C_8)$alkynyl, $(C_1-C_{12})$alkoxy$(C_1-C_{12})$ alkyl, $(C_3-C_7)$cycloalkyl, $(C_3-C_7)$cycloalkyl$(C_1-C_4)$ alkyl, aryl, aralkyl, and heterocyclic$(C_1-C_4)$alkyl;

wherein heterocyclic is selected from the group consisting of 2-,3- or 4-pyridinyl, pyrazinyl, 2-,4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and isoquinolyl optionally substituted with up to two substituents independently selected from $(C_1-C_4)$alkyl, halogen, cyano, nitro and trihalomethyl;

and enantiomers, stereoisomers, and agronomically acceptable salts thereof.

2. The compound of claim 1 wherein R is selected from the group consisting of $(C_1-C_{12})$alkyl and halo$(C_1-C_{12})$ alkyl, $R_1$ is selected from the group consisting of aryl and $C(R_6R_7R_8)$, and $R_4$ is selected from the group consisting of trihalomethylsubstitutedphenyl and halo-substituted phenyl.

3. The compound of claim 2 wherein R is $(C_1-C_4)$alkyl, $R_1$ is selected from the group consisting of phenyl, halo-substituted phenyl, and $C(R_6, R_7, R_8)$, and $R_4$ is selected from the group consisting of 2-chlorophenyl, 2-fluorophenyl, 2-trifluoromethylphenyl, 3-chlorophenyl, 3-fluorophenyl, 3-trifluoromethylphenyl, 4-chlorophenyl, 4-fluorophenyl, 4-trifluoromethylphenyl and 2,4-dichlorophenyl.

4. The compound of claim 2 wherein R is $(C_1-C_4)$alkyl, $R_4$ is selected from the group consisting of 2-chlorophenyl, 2-fluorophenyl, 2-trifluoromethylphenyl, 3-chlorophenyl, 3-fluorophenyl, 3-trifluoromethylphenyl, 4-chlorophenyl, 4-fluorophenyl, 4-trifluoromethylphenyl and 2,4-dichlorophenyl, and $R_6$, $R_7$ and $R_8$ are each independently selected from the group consisting of hydrogen and $(C_1-C_4)$ alkyl.

5. The compound of claim 3 wherein R is methyl, $R_1$ is selected from the group consisting of phenyl, 2-chlorophenyl, 3-chlorophenyl, 4-chlorophenyl, and $R_4$ is selected from the group consisting of 4-chlorophenyl, 4-fluorophenyl, 4-trifluoromethylphenyl and 2,4-dichlorophenyl.

6. The compound of claim 4 wherein R is methyl, $R_4$ is selected from the group consisting of 4-chlorophenyl, 4-fluorophenyl, 4-trifluoromethylphenyl and 2,4-dichlorophenyl, and $R_6$, $R_7$, and $R_8$ are hydrogen.

7. The compound of claim 5 wherein $R_1$ is selected from the group consisting of phenyl and 4-chlorophenyl, $R_4$ is selected from the group consisting of 4-chlorophenyl and 4-fluorophenyl.

8. The compound 5-(4-chlorophenyl)-2,3-dimethyl-3-(3-pyridyl)isoxazolidine.

9. A fungicidal composition for controlling phytopathogenic fungi which comprises an agronomically acceptable carrier and the compound of claim 1 wherein the ratio of the carrier to the compound is between 99:1 and 1:4.

10. A method for controlling phytopathogenic fungi which comprises applying the compound of claim 1 to the locus where control is desired, at a rate of from 0.005 to 50 kilograms per hectare.

* * * * *